US012605514B2

(12) United States Patent
Taylor et al.

(10) Patent No.: US 12,605,514 B2
(45) Date of Patent: Apr. 21, 2026

(54) VASCULAR ACCESS METHODS

(71) Applicant: X9, Inc., Wallingford, CT (US)

(72) Inventors: Eric Taylor, West Harford, CT (US); Brock Kopp, Garden City, ID (US); Alok Agrawal, New Haven, CT (US); Sean Casley, Branford, CT (US); Pablo Acosta, Newark, CA (US); Russell Pribanic, Roxbury, CT (US); Earl Bright, II, Sunnyvale, CA (US); Jonathan Podmore, San Carlos, CA (US)

(73) Assignee: X9, Inc., Wallingford, CT (US)

( * ) Notice: Subject to any disclaimer, the term of this patent is extended or adjusted under 35 U.S.C. 154(b) by 0 days.

(21) Appl. No.: 19/257,653

(22) Filed: Jul. 2, 2025

(65) Prior Publication Data

US 2025/0345025 A1     Nov. 13, 2025

Related U.S. Application Data

(63) Continuation of application No. PCT/US2025/014834, filed on Feb. 6, 2025.

(Continued)

(51) Int. Cl.
*A61M 5/42*          (2006.01)
*A61B 8/00*          (2006.01)
(Continued)

(52) U.S. Cl.
CPC .............. *A61M 5/427* (2013.01); *A61B 8/06* (2013.01); *A61B 8/0841* (2013.01); *A61B 8/085* (2013.01);
(Continued)

(58) Field of Classification Search
CPC ......... A61B 8/085; A61B 8/06; A61B 8/4444; A61B 8/4488; A61B 8/466; A61B 8/488; A61B 8/0841; A61B 8/0891; A61B 8/14; A61B 8/42; A61B 8/4477; A61B 8/4494; A61B 8/461; A61B 8/5223; A61B 8/54; A61B 17/3403; A61B 2017/3413; A61B 2560/0487; A61M 5/427; A61M 5/158; A61M 5/3655; A61M 2205/1585; A61M 2205/1588; A61M 2205/3327; A61M 2205/3375; A61M 2205/502;
(Continued)

(56) References Cited

U.S. PATENT DOCUMENTS 8,951,195 B2     2/2015  Sheldon et al.
9,743,875 B2     8/2017  Maguire et al.
(Continued)

OTHER PUBLICATIONS

He et al., A ventipuncture robot with decoupled position and attitude guided by near-infrared vision and force feeback, Int J Med Robot, Nov. 2, 2022, pp. 1-12, John Wiley & Sons Ltd., wileyonlinelibrary. com/jornal/rcs.
(Continued)

*Primary Examiner* — Chao Sheng

(57) ABSTRACT

Systems and methods for delivering needles or catheters within target tissue including an apparatus that includes or a method involving, structure configured for placing a needle, a catheter or a cannula to provide vascular access. In one or more approaches, a vascular access device or system is provided for hemodialysis.

13 Claims, 25 Drawing Sheets

Related U.S. Application Data

(60) Provisional application No. 63/669,094, filed on Jul. 9, 2024, provisional application No. 63/645,725, filed on May 10, 2024.

(51) Int. Cl.

| | |
|---|---|
| *A61B 8/06* | (2006.01) |
| *A61B 8/08* | (2006.01) |
| *A61B 8/14* | (2006.01) |
| *A61B 17/34* | (2006.01) |
| *A61M 1/36* | (2006.01) |
| *A61M 5/158* | (2006.01) |
| *G16H 10/60* | (2018.01) |
| *G16H 20/40* | (2018.01) |
| *G16H 30/40* | (2018.01) |
| *G16H 40/63* | (2018.01) |
| *G16H 50/20* | (2018.01) |
| *G16H 50/50* | (2018.01) |

(52) U.S. Cl.
CPC .............. *A61B 8/0891* (2013.01); *A61B 8/14* (2013.01); *A61B 8/42* (2013.01); *A61B 8/4444* (2013.01); *A61B 8/4477* (2013.01); *A61B 8/4488* (2013.01); *A61B 8/4494* (2013.01); *A61B 8/461* (2013.01); *A61B 8/466* (2013.01); *A61B 8/488* (2013.01); *A61B 8/5223* (2013.01); *A61B 8/54* (2013.01); *A61B 17/3403* (2013.01); *A61M 1/3661* (2014.02); *A61M 5/158* (2013.01); *G16H 10/60* (2018.01); *G16H 20/40* (2018.01); *G16H 30/40* (2018.01); *G16H 40/63* (2018.01); *G16H 50/20* (2018.01); *G16H 50/50* (2018.01); *A61B 2017/3413* (2013.01); *A61B 2560/0487* (2013.01); *A61M 1/3655* (2013.01); *A61M 2005/1585* (2013.01); *A61M 2005/1588* (2013.01); *A61M 2205/3327* (2013.01); *A61M 2205/3375* (2013.01); *A61M 2205/502* (2013.01); *A61M 2205/583* (2013.01)

(58) Field of Classification Search
CPC .......... A61M 2205/583; A61M 1/3361; A61M 1/3655; G16H 10/60; G16H 20/40; G16H 30/40; G16H 40/63; G16H 50/50; G16H 50/20

See application file for complete search history.

(56) References Cited

U.S. PATENT DOCUMENTS

| | | | |
|---|---|---|---|
| 10,238,327 | B2 | 3/2019 | Harris et al. |
| 10,555,696 | B2 | 2/2020 | Breteau et al. |
| 11,432,801 | B2 | 9/2022 | Kim |
| 11,903,663 | B2 | 2/2024 | Azevedo et al. |
| 11,992,362 | B2 | 5/2024 | Yarmush et al. |
| 12,064,865 | B2 | 8/2024 | Zamani et al. |
| 2005/0101868 | A1 | 5/2005 | Ridley |
| 2006/0241459 | A1 | 10/2006 | Tai |
| 2012/0197132 | A1 | 8/2012 | O'Connor |
| 2012/0220958 | A1* | 8/2012 | Vournakis ........... A61L 26/0066 604/290 |
| 2016/0228122 | A1* | 8/2016 | Brenneman ........ A61B 17/3468 |
| 2019/0029642 | A1* | 1/2019 | De Cicco .............. A61B 8/445 |
| 2019/0336674 | A1* | 11/2019 | Schermeier ......... A61M 1/3643 |
| 2020/0261113 | A1 | 8/2020 | Bagwell et al. |
| 2020/0289845 | A1 | 9/2020 | Martinez et al. |
| 2020/0338309 | A1 | 10/2020 | Kopperschmidt et al. |
| 2021/0045711 | A1 | 2/2021 | Brattain et al. |
| 2021/0378627 | A1 | 12/2021 | Yarmush |
| 2022/0354399 | A1 | 11/2022 | Overbeeke et al. |
| 2023/0008419 | A1 | 1/2023 | Wilson et al. |
| 2023/0200847 | A1 | 6/2023 | Barton et al. |
| 2023/0404529 | A1 | 12/2023 | Colley et al. |
| 2024/0138806 | A1 | 5/2024 | Inukai et al. |
| 2024/0180523 | A1* | 6/2024 | Bappoo ................. A61B 8/488 |
| 2025/0073398 | A1 | 3/2025 | Narrow et al. |

OTHER PUBLICATIONS

Xinru et al.,Application and development of intravenous puncture robot system,Hans Journal,Feb. 2023, vol. 12 No.1, Hans Press, open access.

* cited by examiner

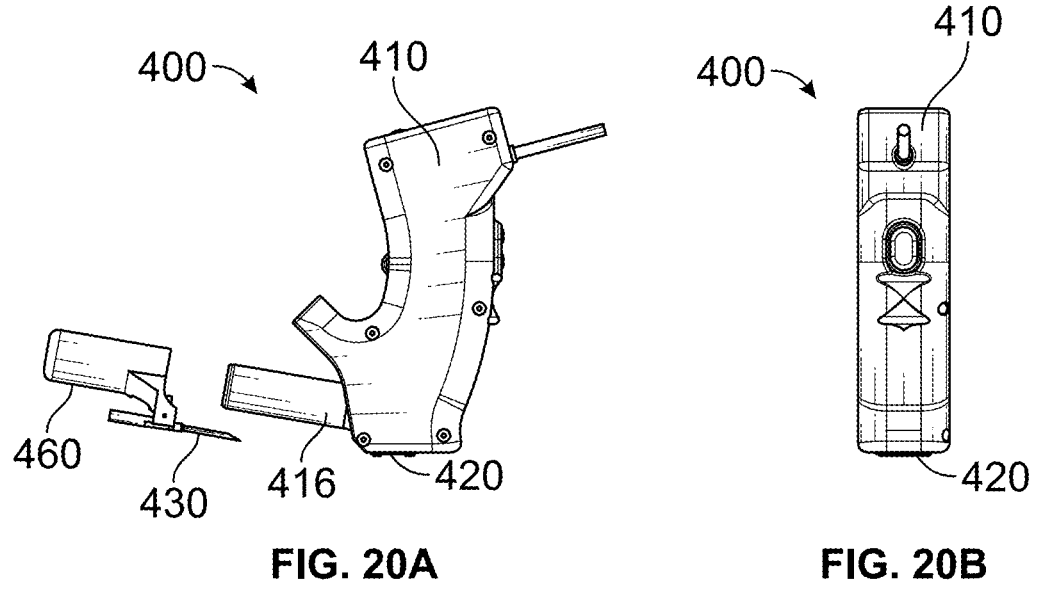
FIG. 20A
FIG. 20B
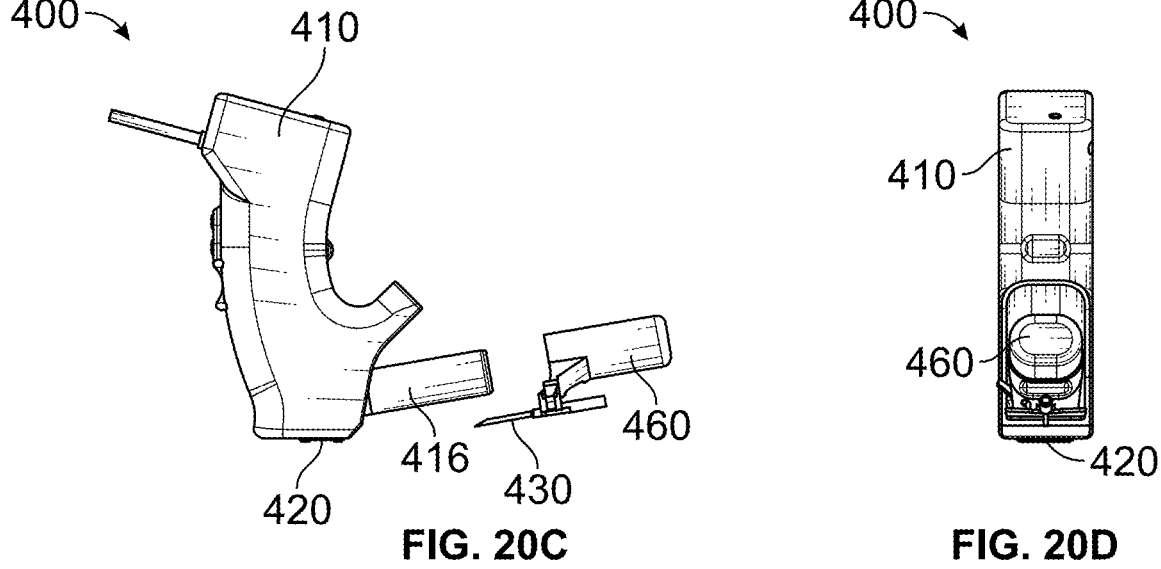
FIG. 20C
FIG. 20D

FIG. 20E          FIG. 20F

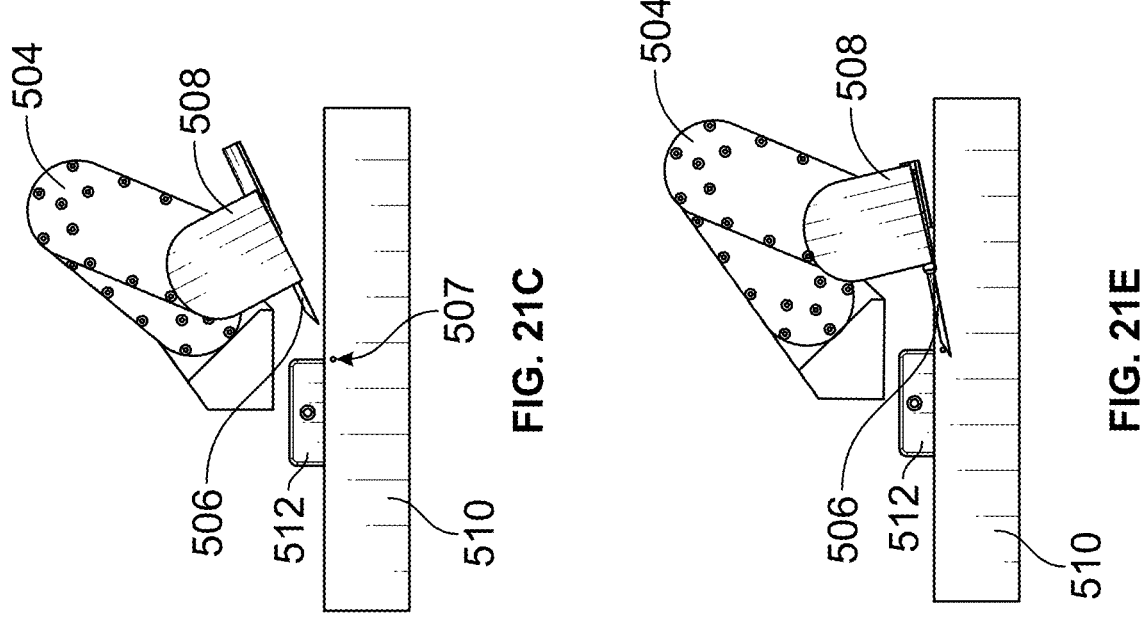
FIG. 21B
FIG. 21C
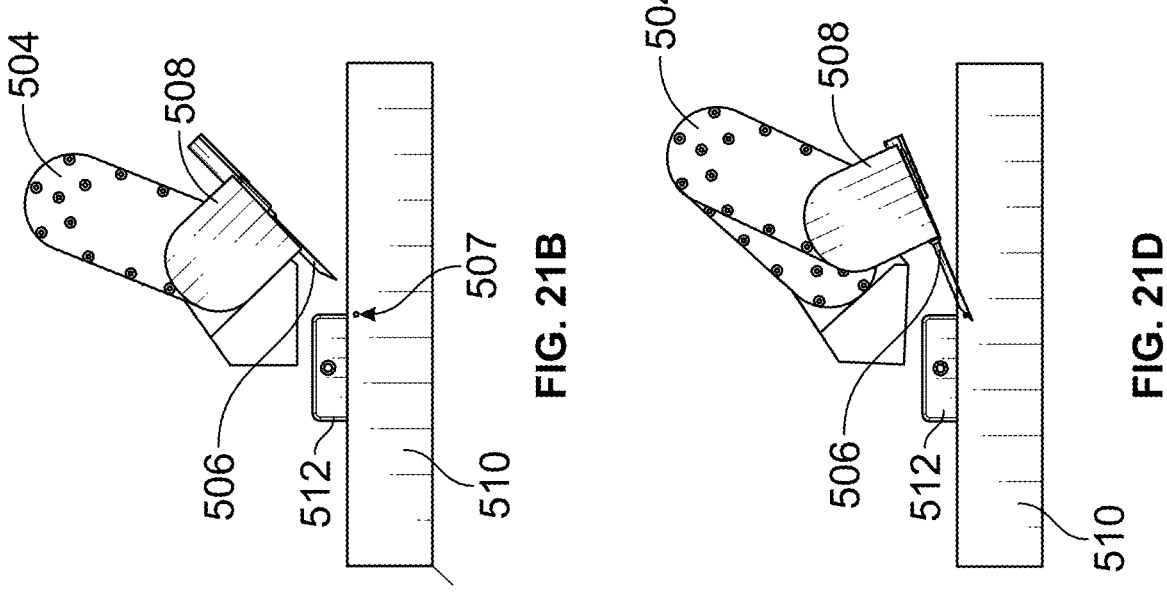
FIG. 21D
FIG. 21E

VASCULAR ACCESS METHODS

FIELD OF THE DISCLOSURE

The present disclosure generally relates to systems and methods to deliver needles or catheters within target tissue, vasculature or grafts.

BACKGROUND OF THE DISCLOSURE

There is a continuing need for an effective alternative approach for needle or catheter delivery and in particular for hemodialysis vascular access. Moreover, there is a need for an access system for clinic or home use which is easy and effective to use.

Hemodialysis has become a conventional approach to treat individuals with kidney disease. A hemodialysis procedure, commonly referred to as dialysis, involves filtering wastes from a person's blood and thus supports or replaces biological functions provided by a healthy kidney. Effective dialysis results in facilitating balancing substances residing in blood including calcium, potassium and sodium, and also can aid in controlling blood pressure.

Typically, a hemodialysis treatment lasts about four hours and is conducted three times per week, but more frequent and longer treatments can be necessary for some patients. Adding to this, the time to travel to a treatment center and waiting to be hooked up and disconnected from a dialyzer of course adds up to a very significant commitment from the patient both in time and effort.

Hemodialysis treatment is a life sustaining treatment that is performed three times per week until a patient can receive a kidney transplant. With the severe shortage of kidneys available relative to the number of end stage renal disease patients, most patients will be on three day per week hemodialysis for the rest of their life. Therefore, there is a need for a system that assesses the health of their arteriovenous fistula or graft, and assists with determining where needle insertion should be each treatment to help provide longevity of the usability of that fistula or graft. Also, there is a need to detect, earlier than a person can using standard of care techniques, when a problem such as stenosis or thrombosis is developing.

It is due to these limitations associated with dialysis performed at treatment centers that more efficient hemodialysis including cannulation has become a desirable alternative either in the treatment center or at home. It is thus desirable to make dialysis as well as assessment of desired locations of needle insertion sites and cannulation itself more efficient and/or require less skill. Studies have shown that home dialysis five to seven times a week has dramatically better outcomes in many ways including a longer life and better survival. When dialysis is performed at home, there is no need to travel to a dialysis center. There is also more flexibility in home dialysis as the patient is able to choose a convenient time for dialysis and has a greater sense of control from being independent and doing treatments themselves.

However, unless in-home care staff is engaged, there is most often no medical professional in the home setting to monitor treatments or answer immediate questions. Also, significantly, in the treatment center health care professionals are often busy managing tasks and are less available to assist with or perform the cannulation techniques according to best practices required to insert needles within patient vessels so that the patient can be hooked up to a dialyzer. Cannulation is a skilled nursing task. Also, cannulation and self-cannulation can be a daunting task for many dialysis technicians and patients and many dialysis technicians and patients can lack the necessary dexterity or skill to repeatably, effectively and efficiently chose insertion locations and insert needles to gain access to vasculature through insertion sites. Since proper repeatable cannulation is so critical to successful hemodialysis and the avoidance of infection and other complications, unassisted home dialysis is not currently a practical alternative to large populations of patients.

Hemodialysis is a procedure done tens of thousands of times a day to help people suffering from kidney dysfunction. As a part of the system to replicate the function of (non or low performing) kidney, blood must be removed from the patient, passed through a dialysis machine to clean it of wastes, salts, and fluids, and then have the blood returned to the patient. To facilitate the path of blood through a dialysis machine, two connections or cannulations must be made to the patient. These connections are large bore needles delivered by dialysis technicians who have a wide range of skill and experience. Preferably, there would be a system or machine that would enable all technicians, or even patients, to safely, reliably, deliver these needles and make the connections without causing any issues or damage to the target vessels. To achieve this goal, an ultrasound-assisted vascular access system is desired.

Prior art systems have focused on vascular access in emergency situations that just require identifying a needle insertion location one time and guiding insertion of the needle to that one location, usually a femoral artery or vein, the internal jugular vein, or subclavian artery or vein.

Accordingly, there is a need for effective and efficient devices and approaches to delivering needles or catheters and for minimizing or reducing the time involved in receiving hemodialysis, as well as for doing so in a treatment center or home setting with simple-to-use systems that help to minimize trauma and infection, and assess and monitor fistula or graft patency and health.

There is also a need to simplify and automate workflow both for the dialysis technician and the patient who is undergoing dialysis. These approaches should be associated with predictable results and be relatively easy to employ.

The present disclosure addresses these and other needs.

SUMMARY OF THE DISCLOSURE

Briefly and in general terms, the present disclosure is directed towards a device or system that eases and standardizes the safe placement of needles or catheters for dialysis. Additionally, there are many other opportunities for automatic, guided, needle or catheter delivery so that the present disclosure also provides a system that would have many other applications beyond dialysis.

In one aspect, there is provided a portable, handheld electromechanical device which assists with or enables needle or catheter insertion for vascular access in hemodialysis patients. The device may include an imaging modality in the form of a point of care ultrasound. In some embodiments, a display for the user presenting them with the information on location of the identified fistula vessel. Furthermore, an embodiment of the device may include a bi-plane transducer arrangement in which the fistula vessel can be seen in two different planes offset from each other, and as such providing information on the directionality of the vessel. Moreover, the bi-plane approach also allows for the target to be viewed at the spot where the needle enters the vessel and the spot where it is expected to stop, thus providing a clear view of the anatomy from a static position.

Each of these planes are composed of many ultrasound transducer elements which are used to build separate B-mode ultrasound images.

In one embodiment, the system includes an electromechanical embedded device including motors, sensors (a combination of position, current, force or torque, flashback, acoustic sensing with optionality for further expansion of the sensor suite) and a computer. The system also has an inertial measurement unit that allows for the system to measure velocity and acceleration in all directions during use. The computer can be responsible for acquisition of the ultrasound image stream, executing image processing algorithms and finally calculating the inverse kinematics and path planning with all inputs to generate reference trajectories for the cannulation module.

Accurate and reliable cannulation of the needle or catheter in the bloodstream is of paramount importance to avoid complications and prolong the life of the surgically created arteriovenous (AV) fistulas (AVF) and grafts (AVG) in patients for hemodialysis access. Ultrasound guided cannulation can be particularly beneficial in cases where a fistula vessel is small or deep, and real-time feedback from ultrasound can reduce needle stick errors, improve accuracy and success rates for hemodialysis access. Accordingly, ultrasound can be utilized in place of or in addition to user observed sound and feel to facilitate building a detailed image for a user, such that subjective user feedback can be proceduralized along with ultrasound imaging to accomplish desired cannulation.

To facilitate this needle or catheter insertion, ultrasound provides inputs to a control module which understands the geometry and capabilities of the delivery device and the intended target. With these two pieces of information a needle path can be determined and applied when the user activates the device for needle insertion. Additionally, the disclosed system or device can continuously monitor the anatomy to ensure that the target is correctly positioned and thus provides a platform that can be used in a dynamic and handheld embodiment.

In one particular aspect, there is provided a combination of detailed geometry and capability as well as mechanical properties such as stiffness of components of the delivery device that are combined with the kinematic analysis to allow a needle insertion system to produce a needle path from a start position to a needle successfully placed in a target vessel.

In another aspect, the vascular access system eases and standardizes the safe placement of needles for dialysis. There is a broad range of user variability, anatomy variation, and daily repetition. All of which points to a need to simplify and automate the workflow both for the technician doing the placement and the patient who is undergoing dialysis. In addition, the use of ultrasound can lead to a more standardized assessment of the patient's anatomy to ensure the vessel/graft health is maintained over time, as well as facilitate observing even small changes in the health of a fistula such as seeing a stenosis develop early or detecting the presence of recirculation or aid in identifying signs of a hematoma or clotting.

These and other features of the disclosure will become apparent to those persons skilled in the art upon reading the details of the systems and methods as more fully described below.

BRIEF DESCRIPTION OF THE DRAWINGS

FIGS. 20A-M are various views, depicting another embodiment of a vascular access device.

FIGS. 21A-E are perspective and side views, depicting yet another embodiment of a vascular access device.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms "a", "an", and "the" include plural referents unless the context clearly dictates otherwise. Thus, for example, reference to "the system" includes reference to one or more systems and equivalents thereof known to those skilled in the art, and so forth.

Figure 1:
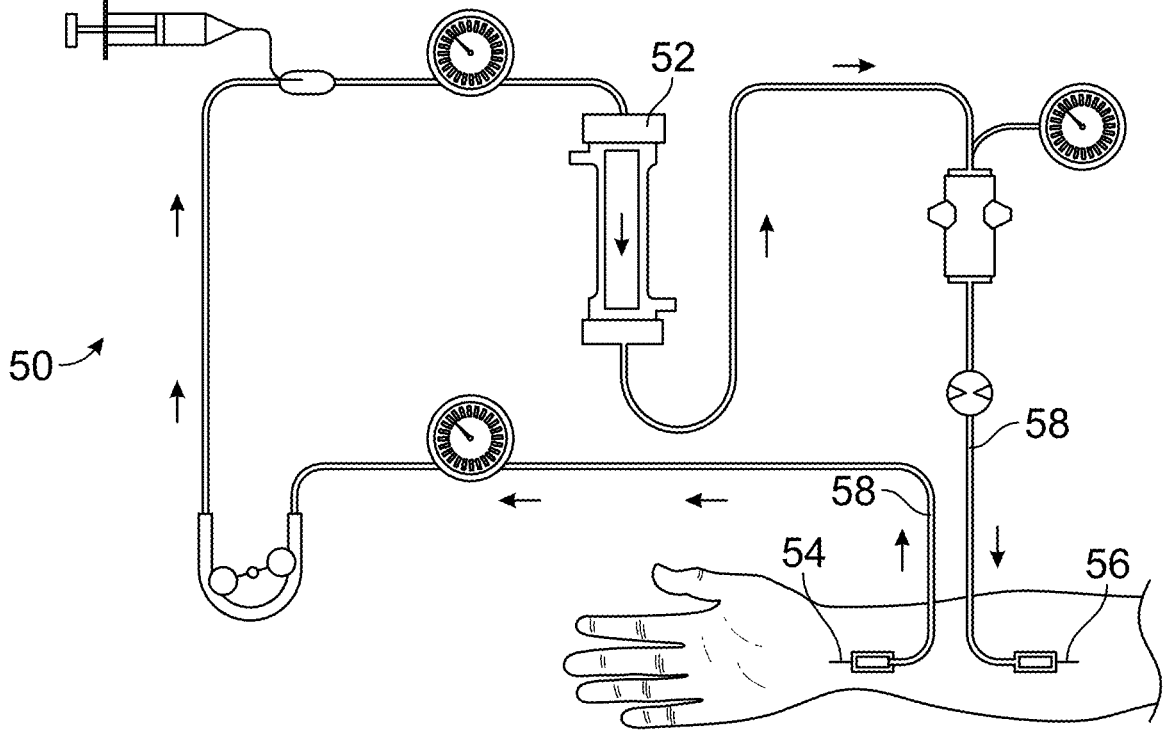
FIG. 1 is a schematic representation, depicting a hemodialysis procedure and equipment.

With reference to FIG. 1, a hemodialysis system 50 and associated equipment is shown. During hemodialysis, the patient's blood is routed through a dialyzer 52 which filters the blood. The patient is prepared by cleaning the sites from which blood flow out and then back into the patient's blood vessels. As described more below, steps are taken to prepare the patient's vasculature for dialysis. Once the patient's vessels are so prepared, at the start of hemodialysis, a pair of needles 54, 56 are inserted into the patient's arm. A numbing compound can be used to facilitate needle insertion and to minimize pain. Each needle is attached to a soft tube or cannula 58 that connects to the dialysis system 50. The dialysis system 50 pumps blood through a dialyzer 52 and returns the blood to the patient's body. During this process, blood pressure and flow rates are monitored and controlled by the dialysis machine thereby controlling the flow of blood through the filter and speed of which blood flows from and to the patient.

As blood enters the filter, it is forced through a large number of thin, hollow fibers. At the same time, a dialysis solution passes in the opposite direction about the fibers. Waste products are thereby removed from blood and carried by the dialysis solution. Filtered blood is then returned to the patient's vasculature. In this way, extra salt, potassium, calcium and fluid is removed from blood.

Figure 2:
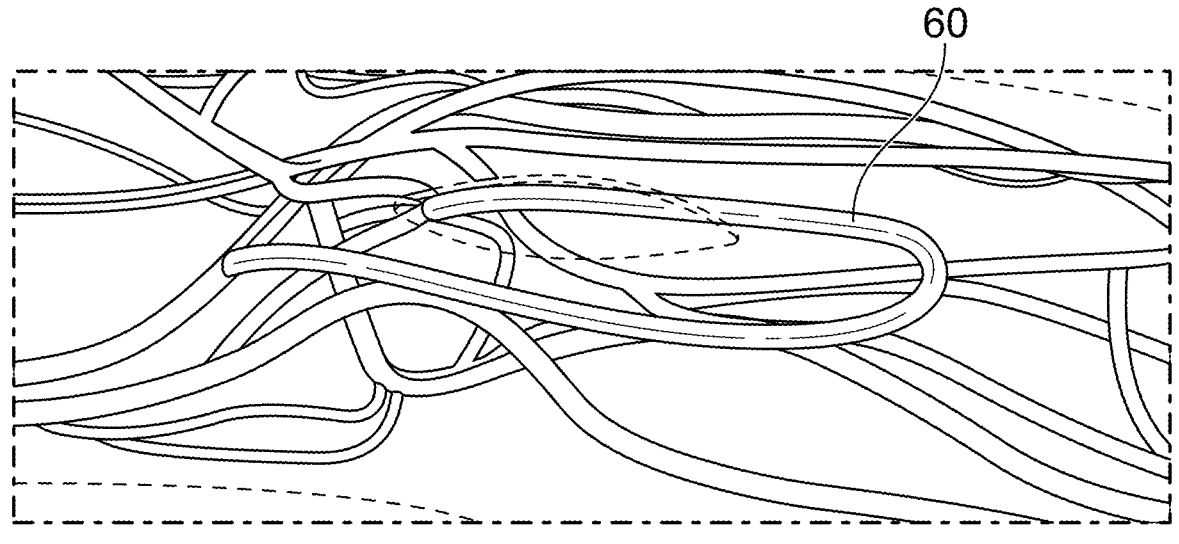
FIG. 2 is a top view, depicting an AV graft in a first vascular access approach.
Figure 3:
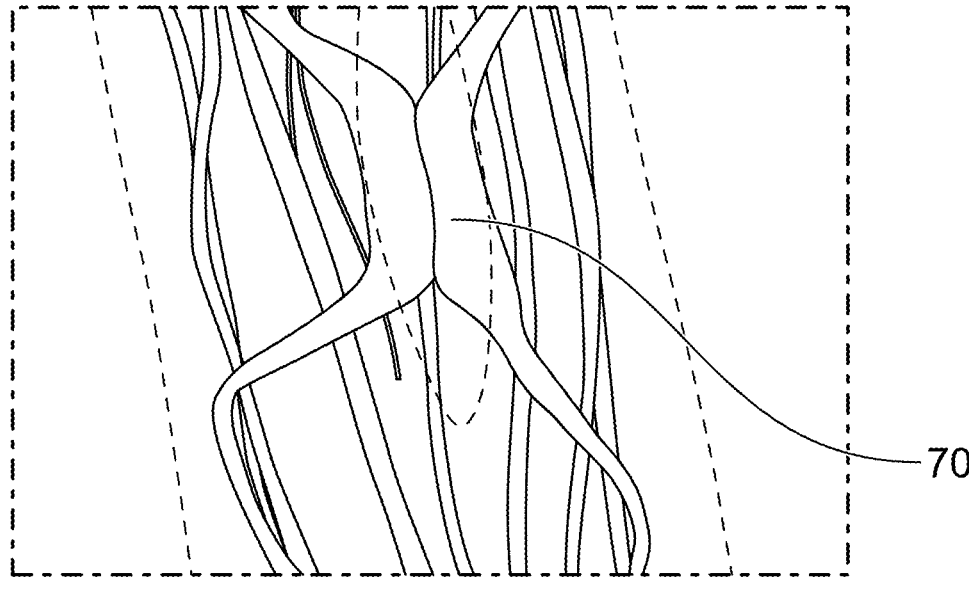
FIG. 3 is a top view, depicting an AV fistula in a second vascular access approach.

An important step before starting hemodialysis treatment is having surgery to create a vascular access site. Vascular access is a phrase used to describe the place on a patient's body where blood flows from and returns to the patient's vasculature such as during hemodialysis. A hemodialysis vascular access site may be a catheter, an arteriovenous (AV) graft 60 (FIG. 2) or an arteriovenous (AV) fistula 70 (FIG. 3). Notably, the catheter approach is generally employed for temporary access and not suited as a permanent solution for home or treatment center dialysis.

To create an AV graft 60 (FIG. 2), during an outpatient procedure, a surgeon cuts the skin to gain access to target vessels. The surgeon then uses a synthetic tube graft 60 to connect an artery which carries blood away from the heart to a vein which carries blood to the heart. The surgical site is then closed, leaving the graft available for dialysis. Dialysis needles are then repeatedly used to access the tube during a hemodialysis procedure as described above. Generally, the AV graft approach is employed for patients that have veins that prevent them from having an AV fistula since the AV graft approach is more often associated with infection and repeated blood clots that can block the flow of blood and make it hard or impossible to have dialysis.

Figure 4:
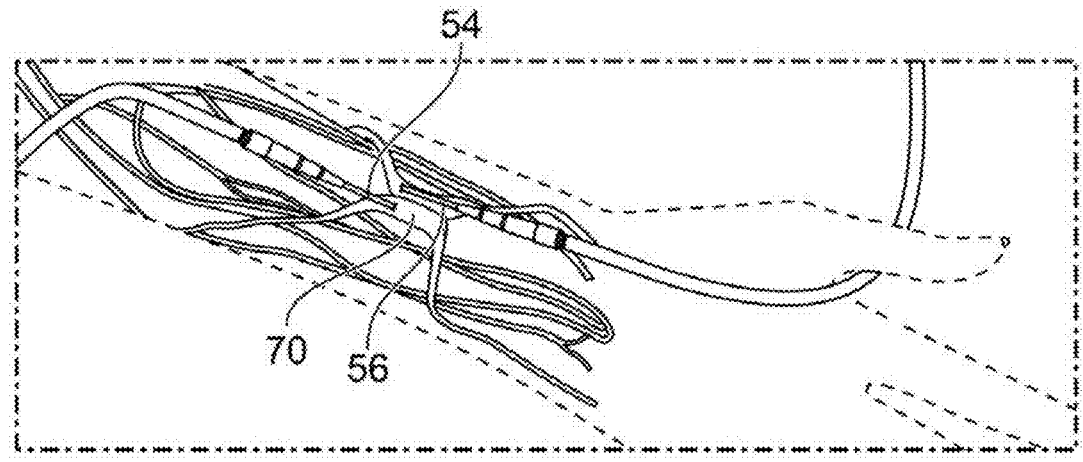
FIG. 4 is a top view, depicting cannulation of the second vascular access approach.
Figure 5:
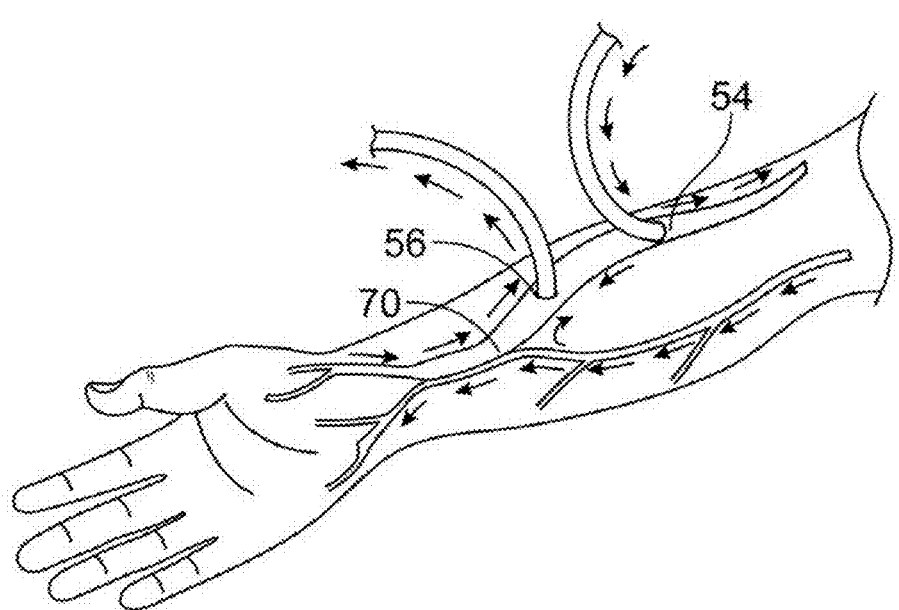
FIG. 5 is a top view, depicting the flow of blood resulting from cannulation.
Figures 6A, 6B, 6C, 6D:
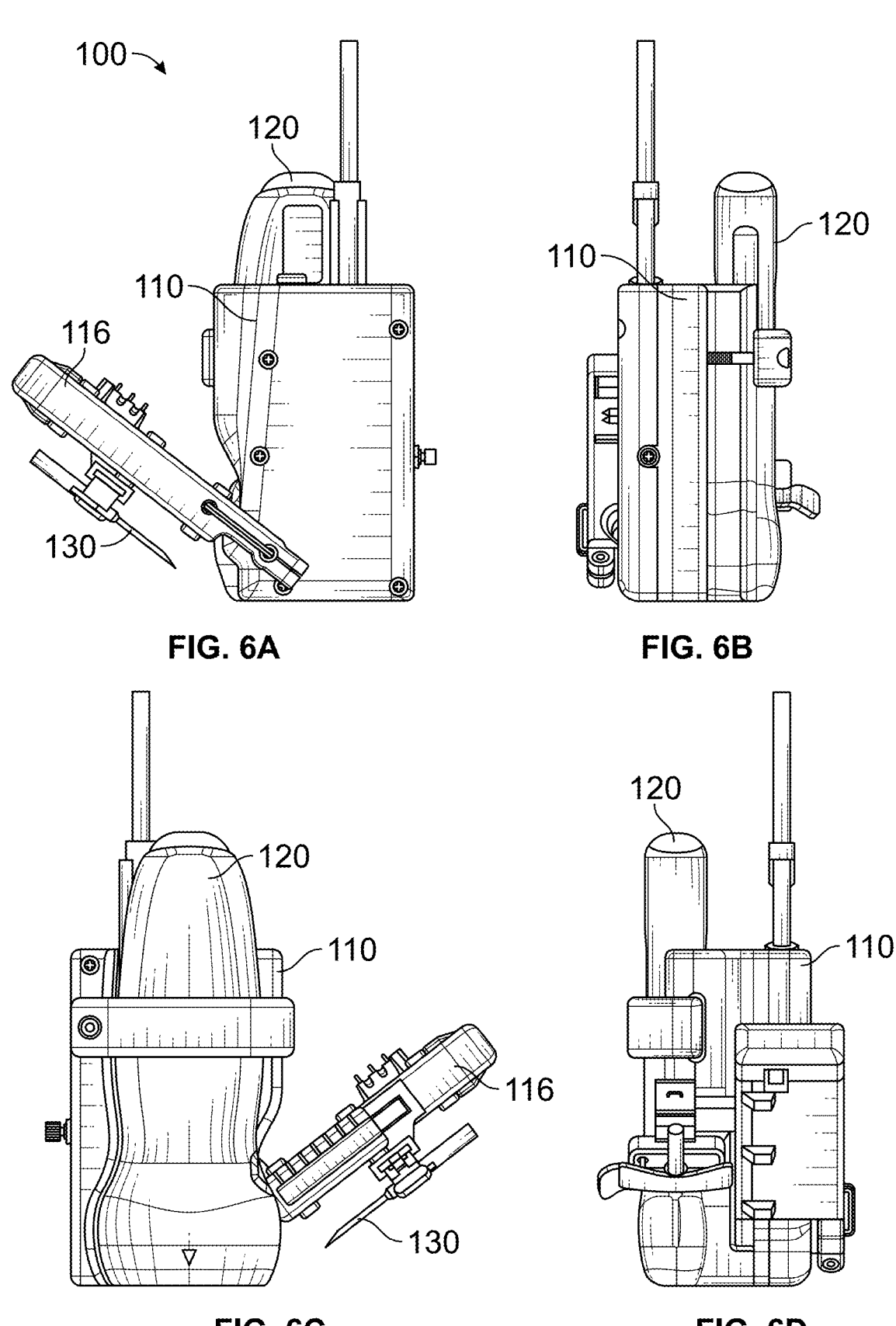
FIGS. 6A-D are various views, depicting one embodiment of a vascular access device.
Figure 7:
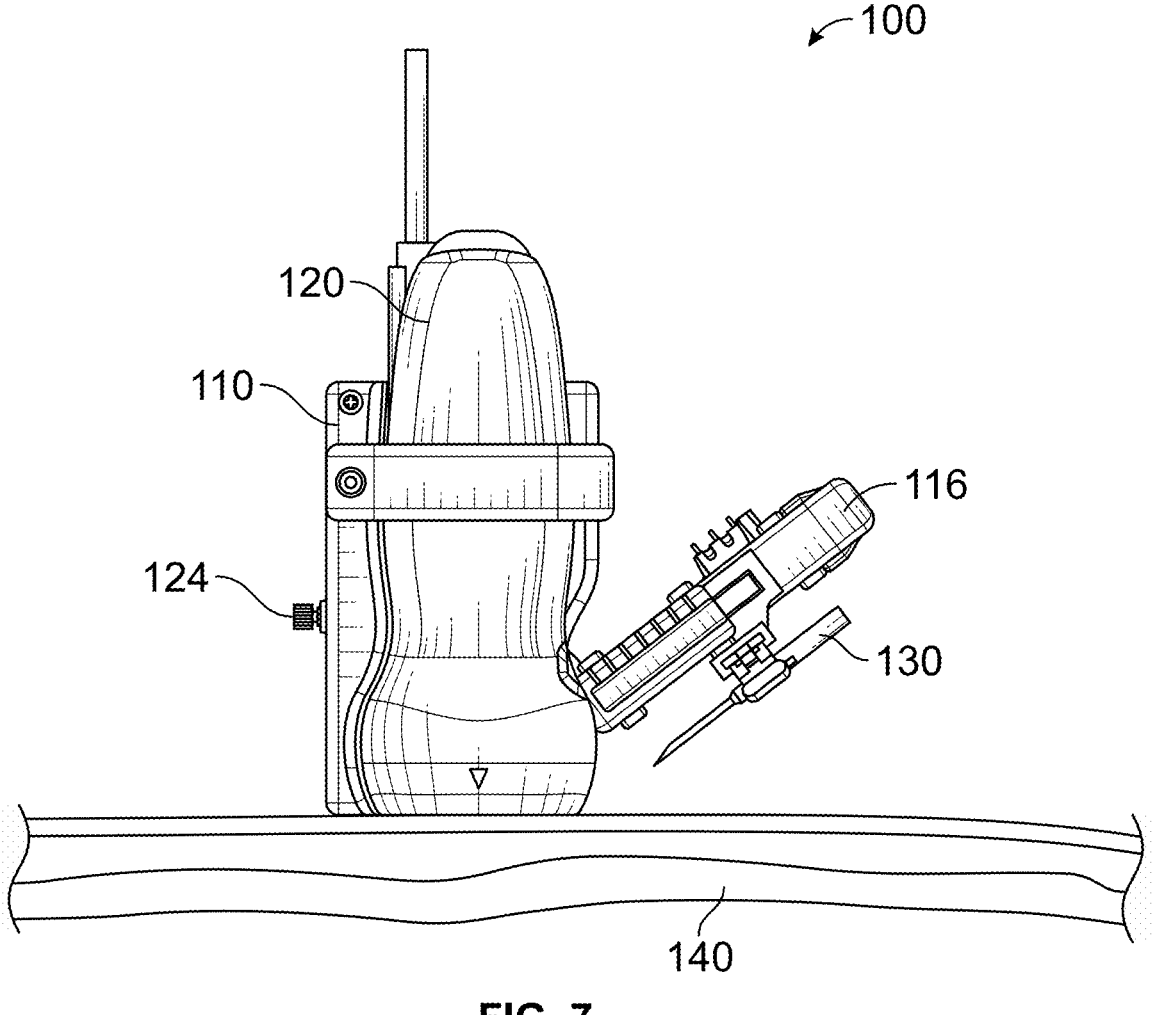
FIG. 7 is a side view, depicting the vascular access device placed against the skin above a target insertion site.

The generally accepted best type of long-term vascular access is an AV fistula 70 (FIG. 3). This approach is characterized as providing the highest blood flow for dialysis, is less likely to become infected or clot, and as lasting longer than other approaches to vascular access. Here, the surgeon connects an artery directly to a vein, usually within the patient's arm, to create the AV fistula. When the vein is so connected to the artery, the vein grows or rather remodels over a number of weeks so that its walls are wider and thicker, making it easier to repeatedly place the needles for dialysis. The AV fistula itself also has a large diameter that allows blood to quickly flow out and back into the patient's body, the goal being creating a system where there is high blood flow so that the largest amount of blood can pass through the dialyzer. FIG. 4 shows the cannulation of two needles 54, 56 at an AV fistula site 70, and FIG. 5 depicts the flow of blood to and from the AV fistula 70 during dialysis. It is to be noted that in using the presently disclosed vascular access systems, any number of treatment protocols can be specified by the treating healthcare professional and embedded into software such that needle cannulation sites may be alternated or rotated in a rope ladder technique or repeatedly used as in the buttonhole technique.

Once the patient is provided with a vascular access site, the challenge becomes placing the needles within the site. In one aspect, the system can manage, but is not limited to, rope ladder or buttonhole site strategies for cannulation as necessary or dictated by the system or health care professional. Accordingly, various approaches to needle delivery methods and apparatus are presented. The disclosed approaches are configured to provide a repeatable, effective and accurate approach to cannulation. The disclosed approaches are intended for use in an in-center setting or a home setting for hemodialysis.

In one embodiment, the system includes an electromechanical embedded device comprising of motors, sensors (a combination of position, current, force, flashback, acoustic sensing with optionality for further expansion of the sensor suite) and a computer. The computer can be in the device or can be separate from the device such as on a cart or the like. In one particular aspect, at least a part of host computing occurs in a cloud-based server. An embodiment of the device can include a mode where the underlying algorithms are continually improving via feedback loop created from the collected data being used as training input. The computer can be responsible for acquisition of the ultrasound image stream, executing image processing algorithms and finally calculating the inverse kinematics and path planning with all inputs to generate reference trajectories for the cannulation module. Further, the computer may comprise a non-transitory computer readable medium comprising instructions to collect and process signals received from data collection devices or functionality or include or communicate with a non-transitory computer readable medium having stored thereon instructions executable by a computing device of the system or external to the system to cause the computing devices to perform functions associated with and directed by the firmware or software. The computer may further comprise instructions to transmit collected and/or processed signals to a memory for storage, or to a module for transmission to another computing device. While the insertion is occurring, the system can also continue to monitor the vessel position, shape, and location and ensure the anatomy or device does not move relative to one another. If it does change the kinematic path accommodates such changes as necessary or halts needle insertion. Thus, real-time control can be provided in that an insertion path is initially calculated and then a safety loop is run in the background looking for changes that may involve a constant analysis of the ultrasound stream of data checking for movement or change. In one particular aspect, there is provided a combination of detailed geometry and capability of the current device combined with the kinematic analysis to allow a needle insertion system to resolve or determine or calculate a needle path from a start position to a needle successfully placed in a target vessel.

Localization of the access can be performed using a machine learning algorithm to identify the access in a B-mode ultrasound image. A B-mode image is a widely used ultrasound display which creates a 2-dimensional grayscale image which represents the echogenicity of tissue under the ultrasound transducer using brightness. Brighter (whiter) pixels represent portions of tissue which reflect ultrasound waves well. Since the blood inside of an access is not echogenic, it shows up as a dark region (often of circular cross section) on the image which is recognized using machine learning. B-mode ultrasound images have the advantage of working when the ultrasound element(s) are at any angle to the blood flow, including perpendicular which is not possible for doppler-based systems. Additionally, since the B-mode image captures a wide plane of tissue, instructions can be communicated to the user to move the device in a certain direction and even a certain distance in order to align the device to an access. This communication can take many forms, including words/numbers, graphic symbols, auditory and/or a simplified representation of the anatomy. While B-mode imaging is primarily used for vessel localization, doppler can be used in addition to B-mode to determine the flow direction, flow velocity, pulsatility, and other characteristics of the blood flow.

The disclosed needle insertion systems are configured and function to position a needle or needles and, in some embodiments, advance the needle within the targeted AV graft, fistula, vessel or vessels. The system further includes functionality for positioning a needle into the correct position and trajectory and, in some embodiments, to advance the needle at a pre-determined angle and depth or along a variable trajectory to a location within a patient's body and within target vasculature. The system is effective for providing vascular access and assists with cannulation throughout the body including specifically for radio-cephalic, brachio-cephalic and brachio-basilic fistulas and use may range from the forearm to the upper arm or other locations on the body. The system can be easily operated in a home setting or in a treatment center and functions to cannulate the patient successfully while improving outcomes and reducing complications. Further, the system can provide access to various anatomical structures that are identifiable via ultrasound such as targeting a biopsy or to gain access to the lymphatic system or the like.

A standard of care is to insert needles for fistulas at 25 degrees, and grafts at 45 degrees. In one or more embodiments, a final insertion angle can be 15 degrees. Therefore, a pivot location is selected such that the portion of a target circle that is utilized to pitch from 45 to 15 degrees is centered at approximately 3 mm deep into the patient because standard for mature fistula access is less than 6 mm depth. This depth could also be adjusted to something other than the average of the possible vessel depths.

One piece of information employed in needle insertion is the identification of a pivot location that is the offset between the pitch axis and the needle axis. This is a detail that is driven by the mechanical design of the device arm and needle holder.

With reference to FIGS. 6A-D and 7, there is shown an embodiment of a vascular access system or handpiece 100 utilizing an external ultrasound probe. The vascular access system includes a body housing 110 containing the mechanical components to alter the pitch of a pivoting arm 116, an attachment to an external ultrasound transducer or probe or array 120, and internal control electronics for both motor control and activation. In addition, connections to both power and a computer run though the body housing 110.

Figure 8:
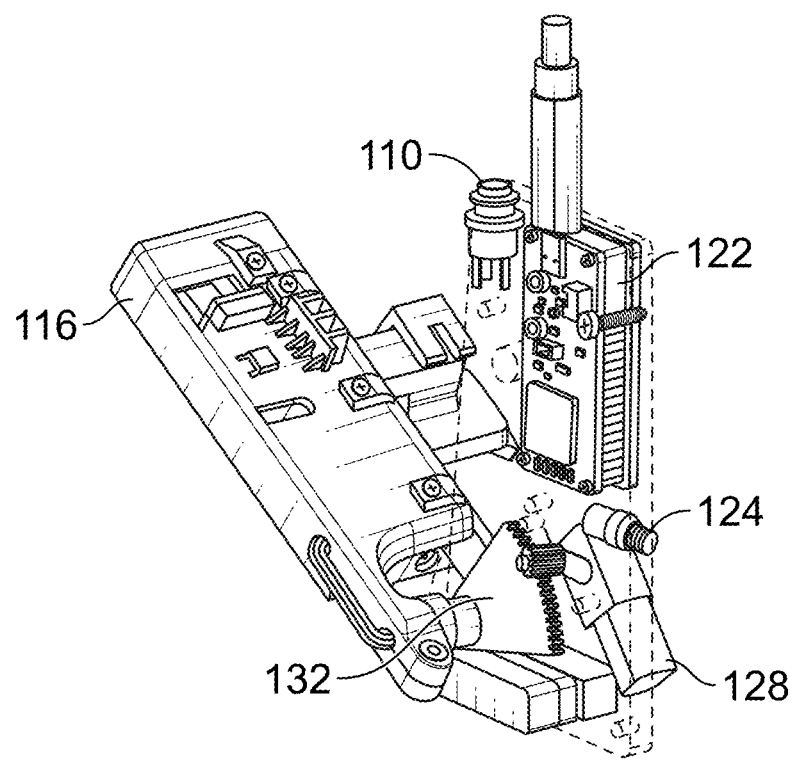
FIG. 8 is a cutaway view, depicting internal components of the vascular access device.

FIG. 8 highlights the internals of the body 110 without the ultrasound array 120 and the body housing 110 shown transparent. It is to be noted that a volume of space can be set aside in the design to stand in for a custom integrated transducer, thus allowing the mechanism for pitch to be designed around the space required for alternative embodiments. Moreover, housed within the body 110 is a controller board 122 that controls the functioning of the system moving components. An activation button 124 is configured to be in electronic communication with the controller 122.

Figure 9:
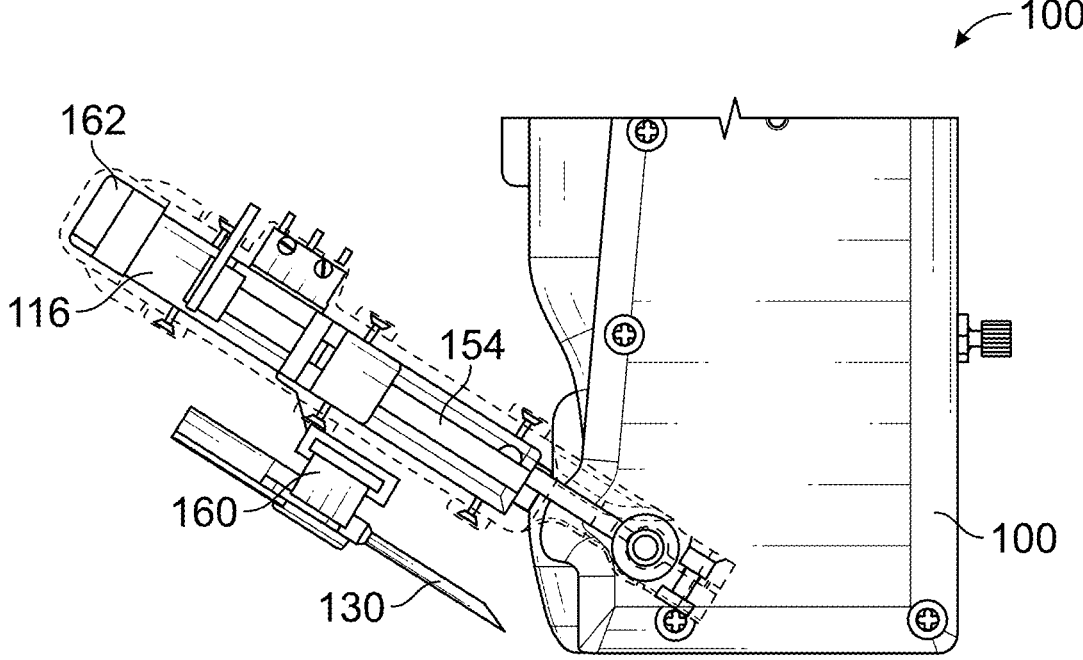
FIG. 9 is a partial cutaway view, depicting internal components of a pivoting arm of the vascular access device.

Mechanically and electronically connected to the body 110 is the pivoting arm 116 (See also FIG. 9). Through a geared transmission, the angle of the arm 116 can be changed via electric (geared, brushed, brushless, stepper, DC) motor 128 mounted within the body 110. Aligning with the traditional guidance for needles entering the AV fistula for hemodialysis, the angle of the arm 116 can range from 0 (parallel to the bottom of the body) to 45 degrees, with likely range for use in the 15 to 45 degrees range. In addition to the pitch control, the pivoting arm 116 has the needle mounting 160 and needle drive systems 162, as detailed in FIG. 9.

In one embodiment, the ultrasound array 120 of the system 100 is rigidly attached or mounted in line with a needle 130. The benefit of attaching to a commercially available ultrasound system both lowers the cost of the vascular access system and allows for a range of ultrasound systems to be used. In one embodiment as described below, an integrated ultrasound array would allow for more refined packaging and better integration of the ultrasound output with the needle application system.

Also provided is a laptop or other computer (not shown). For this embodiment, the current programming and control is from a USB cable attached laptop. Notably, a non-USB cable such as EtherCAT can be used as an alternative, the same facilitating enabling real-time/deterministic communication. In addition to being able to work with the ultrasound images coming to the computer from the ultrasound array, the laptop allows for flexibility in programming and refining the movements of the system 100. In an alternative embodiment, the system 100 could still be attached to a laptop with a fully developed user-interface to allow the laptop/cart to accomplish computational or control work. In yet another embodiment, all the system work can be connected with the electronics within the handheld device requiring only a power connection (or even battery power) to operate. In one aspect, there can be a full integration of processing (computer) function into the device itself.

In terms of automated or robotic systems, the number of controllable motions or actions is a source of complexity and cost. In many cases the additional precision or control needs to be countered by cost in terms of physical parts, manufacturing complexity, or software development/processing burden. The disclosed embodiment distills the design to minimal degrees of freedom so that the system 100 can perform as desired in all conditions of use. Notably, by making the system user controlled or positioned and/or to be easily maneuvered, additional degrees of freedom of motion are inherently provided without additional cost and complexity.

The degrees of freedom present in this embodiment are pitch and insertion. Pitch rotates the needle to a desired insertion angle. Additionally, as the needle advances pitch can be used to alter the needle path angle forward along the target vessel. The combination of these two degrees of freedom allows the system to advance the needle into the target fistula or graft and then adjust to allow the needle to advance along a portion of the length of the fistula or graft, safely, for complete insertion.

In the disclosed embodiment, a range of motion is about 2.5 degrees to about 47.5 degrees with the lower angles for final insertion, such as approximately 15 degrees. As shown in FIG. 8, a brushed DC motor 128 is used to drive a spur or pitch gear 132 and control the angle of pitch. In alternative approaches, brushless DC motors or stepper motors or other types of actuators (piezo motors etc.) can be employed for drive functionality. The motors can further include drive bevel gear trains, belt, capstan plus cable structure, a worm gear or similar drive train to get motion from the motor to the pitch axis. Moreover, a linear actuator can be used to push or pull the pivoting arm 116 offset from a pivot axis.

The angle of the needle 130 for insertion needs to be sensed for the control circuit and such sensing can be provided by a motor encoder (not shown), with a homing step. This would require a drive to a current threshold, torque threshold, or up to a limit switch. Further, an absolute encoder could be used in the device body or arm to measure without a required homing step. Alternatively, a motor driver microchip can be employed where the microchip counts current ripples as the motor turns. As a motor turns, commutations or the electrical connections are made and disconnected multiple times per revolutions. The microchip counts each of these reconnection cycles and calculates the change in position of the motor. In one approach, a magnetic absolute sensor as described below can be used to detect needle position along with ripple counting to verify the motion of the motor plus leadscrew which drives a needle 130.

With reference again to FIG. 7, insertion involves the linear advancement of the needle 130 to the target location. This can be along the angle created/controlled by the pitch. Insertion consists of linear motion to insert the needle 130 into a patient along path to target vessel or location 140. The needle 130 starts outside of patient and is advanced through skin layer, into vessel/target 140. In one embodiment, up to 35 mm of travel is provided. Length of travel is selected to ensure the needle 130 can be held away from the patient to minimize the likelihood of inadvertent needle sticks but close enough to make the insertion fast once the user decides to insert. In various approaches, the needle is protected (i.e. sheathed or covered) until it is needed. In an alternative or additional embodiment, the needle protective structure can be removed by the system itself (rather than the user) as part of a delivery process.

As shown in FIG. 9, in one embodiment, a geared, brushed DC motor 162 is connected to a lead screw 154 to drive a needle holding assembly 160 forward. In alternative approaches, brushless DC motor or stepper motors, as well as compact form factor pneumatics (with a compressor in the cart or stored in a gas cartridge) can be employed. In addition to a lead screw 154, the linear motion could be belt or cable driven, or a linear actuator can be utilized. In this embodiment, the motor 162 is located in the arm 116. In an effort to make the pivoting arm 116 as small and simple as possible, an embodiment could move the motor 162 to the body 110 of the device and have the motor 162 transmit motion by way of a transmission crossing the pivot location. This could be belt, cable, or shaft driven.

Figure 10:
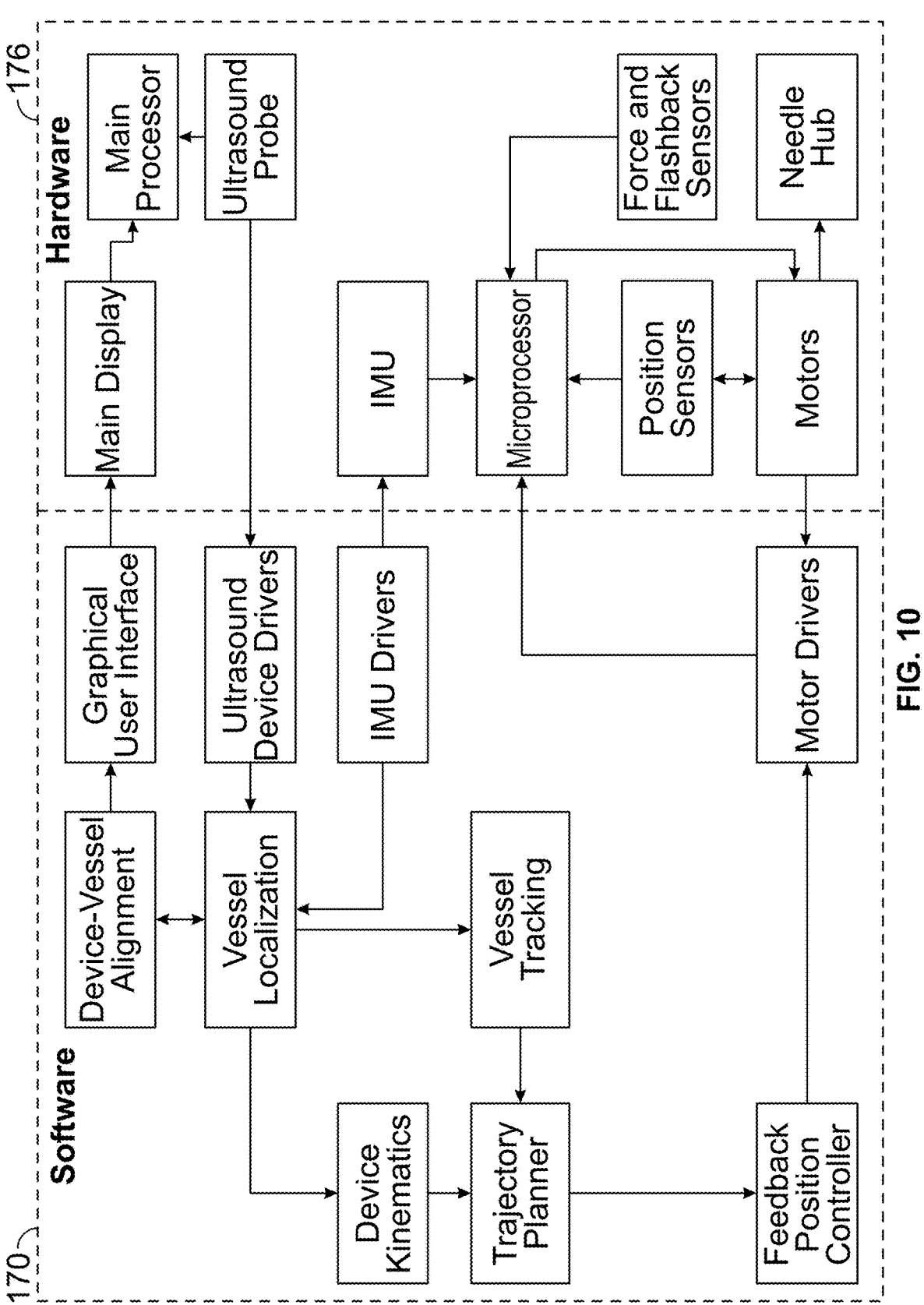
FIG. 10 is a flow chart, depicting a cooperating relationship between software and hardware components of the vascular access device.

With reference to FIG. 10, a needle insertion system 100 involves a cooperation between software 170 and hardware 176 modules. On the software side, code is provided to one or more of accomplish vessel localization, vessel tracking and device-vessel alignment. Vessel localization in turn is based upon sub-programs handling ultrasound device drivers and Inertial Measurement Unit (IMU) driver information. Through communication with a graphical user interface, device-vessel alignment information is communicated to a main display on the hardware side. Software also addresses and makes calculations or assessments concerning, among other things, device kinematics and trajectory planning leading to feedback position control and control of motor drivers. On the hardware side, the main display communicates with a main processor which in turn receives information concerning an ultrasound array. The IMU drivers on the software side communicate with an IMU on the hardware side, and the IMU communicates with a supplemental microprocessor which receives information from force and flashback sensors as well as position sensors and motor driver information transmitted from the software side. The position sensors are additionally in communication with the system motors which are driven to effect positional changes in a needle hub. In another embodiment, the display shows minimal information to the user such as a red light for do not activate and a green light for activate, or even no information to the user but rather provides audible or haptic sensation to direct the user. Additionally, the system can prevent a user from cannulating when certain conditions are met such as a user can only initiate a cannulation when the criteria to display a green light are met (i.e. aligned, stable, etc.). Notably, the needle insertion system is not intended to be affixed to a patient's arm or skin. The IMU is particularly useful as it provides an additional way to determine if a user is moving the handpiece (i.e. needle or catheter or assembly or holder) relative to the patient. In one aspect, checking for motion can be faster than ultrasound images are received and processed to identify motion of the device.

Figure 11:
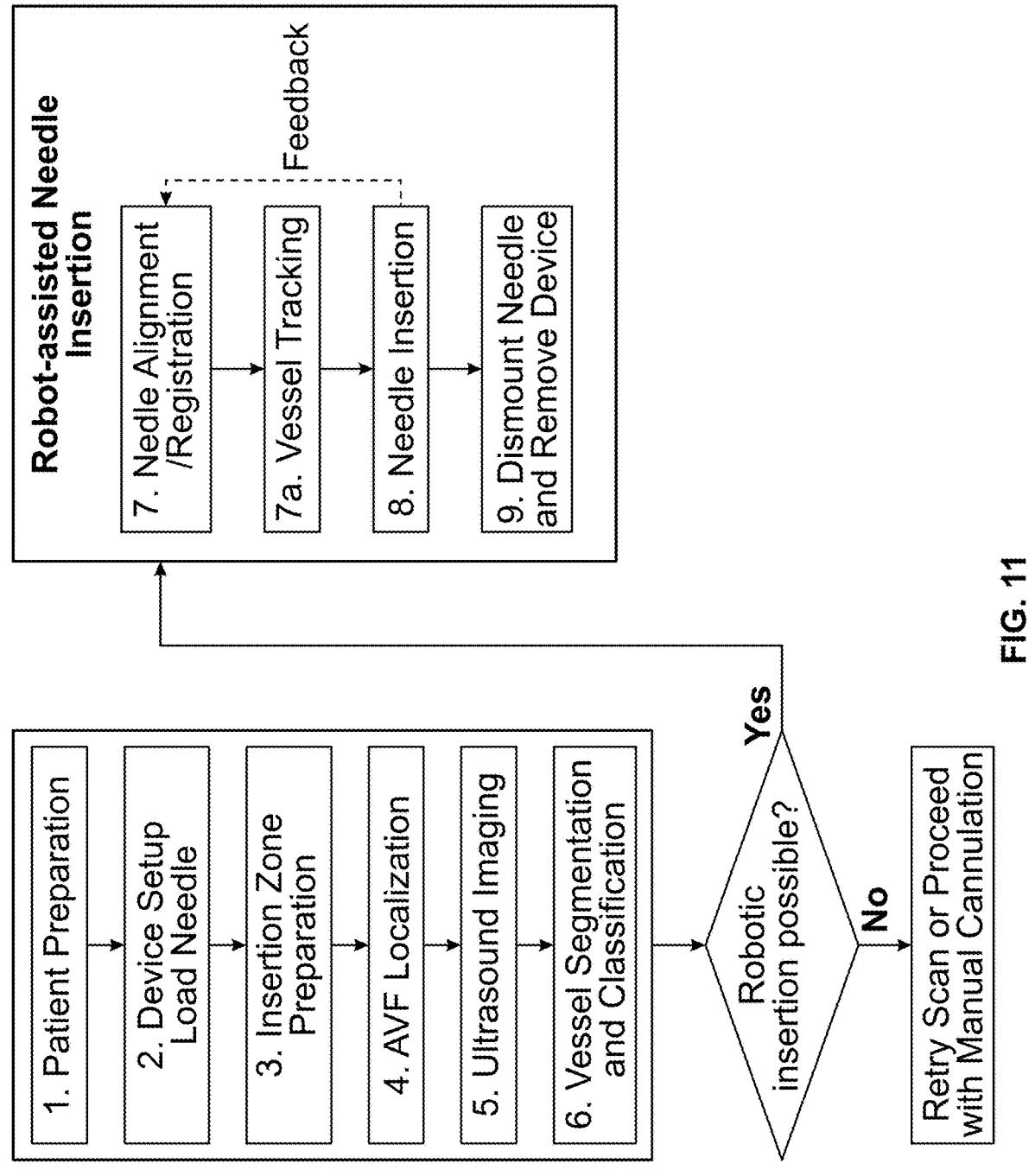
FIG. 11 is a flow chart, depicting a workflow for use of the vascular access device.

Employing the needle insertion system can involve a workflow including one or more of the following steps (FIG. 11). A patient is assessed to determine whether a needle insertion system can be used for cannulation (steps 1-6) by moving the system 100 along the length of, or substantial portion thereof, the fistula or graft to record ultrasound image data. Should it be determined that intervention using the needle insertion system can be employed, a device setup is conducted. If not, the patient can be assessed again using the information learned during a previous assessment. Once it is determined that an individual is a candidate, the needle insertion device or cart associated with the device, which can be plugged into an outlet for charging overnight, is used. The user attaches the needle to the system, ensuring to keep area clean, and removes the needle guard provided with each needle (step 2). In one embodiment, a battery can be provided that is configured to last a working day. Just prior to use, an operator wipes down the needle insertion module for infection control. Next, the user cleans the area selected for cannulation (step 3). One or more of AVF localization, ultrasound imaging and vessel segmentation and classification are conducted on the anatomy of the patient (Steps 4-6). Fistula health is assessed and the system logs data for trending and prediction of patient access issues. The system can identify a patient by scanned fistula anatomy and pulls up the patient record. Records can be stored locally or on the cloud, from which assessment of fistula and guidance for next treatments are stored. The record and system direct the user to a next location on the patient using reference from previous cannulation history. In addition, measurements of the fistula can be made with both ultrasonic imaging as well as flow assessment based on doppler scanning.

Once the patient is registered, or alternatively without registering the patient, the user places the needle insertion device on a patient's arm near where they want to cannulate (step 7). The needle is loaded with a protective cover in place. The protective cover is removed from the needle after the needle is attached to the needle holder and the user is ready to place the device on the patient's skin. Using the ultrasound array, the user guides the needle insertion device to be centered on and aligned to the target vessel (fistula or graft; step 7b). Ultrasound interface material (gel or other) is employed for visualization. Once aligned to the user's satisfaction, user activates needle insertion, likely through pressing the activation button (step 8). Notably, the system can use its sensors to choose not to insert the needle even if commanded by the user such as by pressing the button. Here, the system could use the ultrasound alignment information to make this decision, or could use the IMU position velocity data, or other sensors. The needle insertion system is nevertheless configured to insert and advance the needle through the skin and to the target vessel. During the motion, the system can adjust needle angle during advancement to ensure needle is both in the vessel but not contacting vessel walls. Once complete and before moving the cannulation module, the user releases the needle (step 9). The needle will then be taped and secured to the patient. User repeats steps for placement of a second needle.

Figure 12:
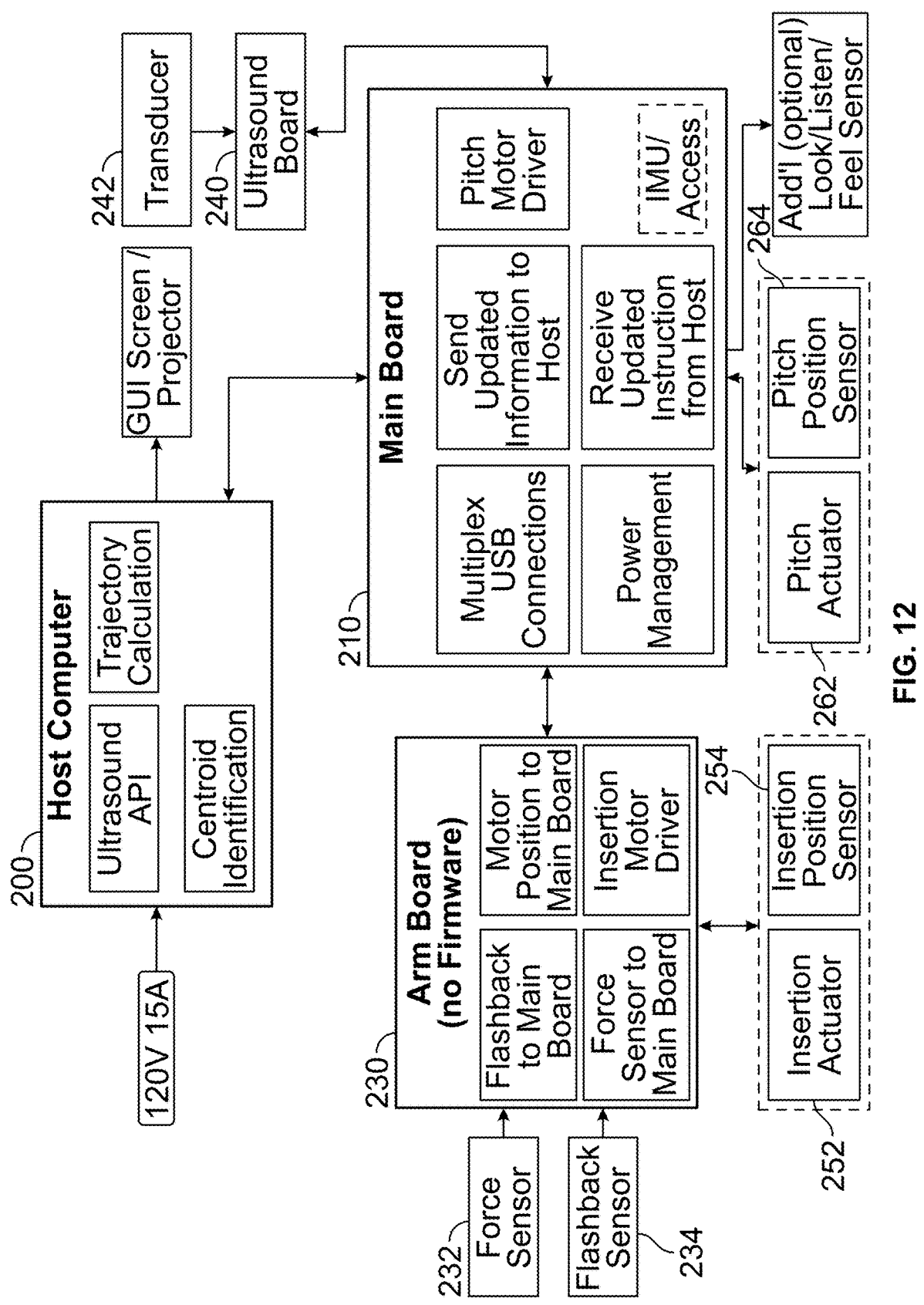
FIG. 12 is a schematic, depicting computer communication of the vascular access device.

Turning now to FIG. 12, there is provided a schematic depicting the relationships and connections between a computer (laptop) 200, main board (located in the body) 210, and motors and sensors. In alternative embodiments, the various connections and processing can be moved between the various platforms or isolated to a single platform. The main board 210 is in communication with both an arm board 230 which controls the pivoting arm 116 and that communicates with a force sensor 232 and a flashback sensor 234, and an ultrasound board 240 that communicates with a transducer 242. The force sensor 232 is associated with and provides information concerning needle penetration into tissue, and the flashback sensor 234 is associated with and provides information concerning blood flashback within a needle. Two-way communication is further provided between the arm board 230 and an insertion actuator 252 and an insertion position sensor 254, and between the main board 200 and a pitch actuator 262 and a pitch position sensor 264. The insertion actuator 252 operates to actuate insertion or movement of a needle during a use procedure and the position sensor 254 is associated with and provides information concerning a position of a needle within space or relative to target tissue. Further, the pitch actuator 262 operates to actuate pitch control, and the position sensor 264 is associated with and provides information concerning needle positioning relative to target tissues or generally within space.

Figures 13A, 13B:
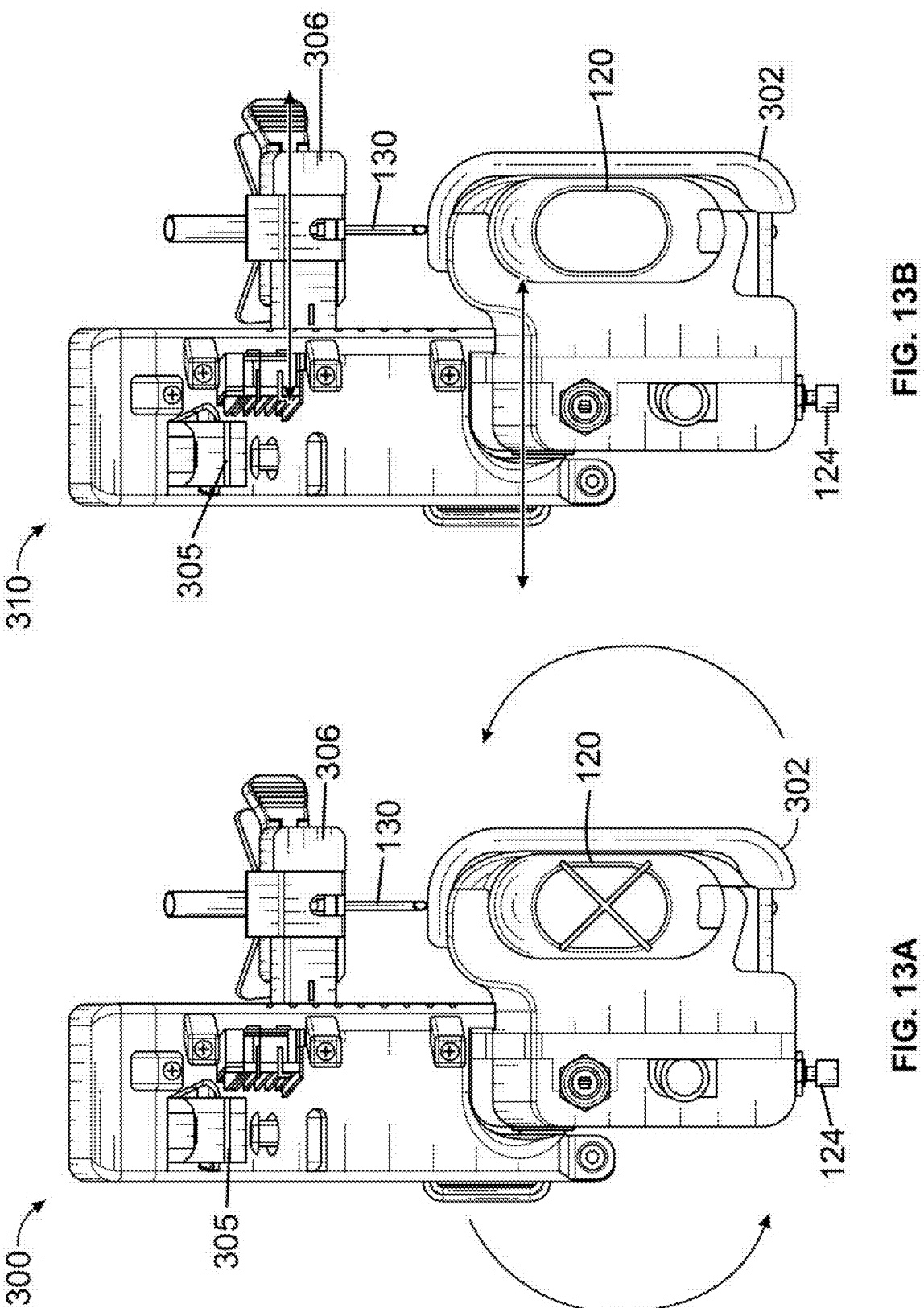
FIGS. 13A-B are top views, depicting alternative approaches to a vascular access device.

In alternative approaches, additional degrees of freedom and control can be provided to make needle placement as easy and efficient as possible. In one embodiment, a system 300 (FIG. 13A) can be configured or include structure arranged to additionally provide a rotation of the ultrasound housing 302 with respect to a pitch arm housing 300 which can be useful in facilitating the device to adjust and approach the target vessel in a direction as parallel as possible. Notably, the pitch arm housing 302 includes an insertion motor that functions to drive the needle 130 that is attached to a needle holder 306. This also allows for the elimination of the user having to align the device or handpiece 300 to the vessel. In one approach, a ring gear (not shown) can be configured at a base of the device 300, driven by a motor and spur gear. A likely beneficial amount of movement can be about 5 to about 15 degree rotation, but up to 30 degrees would give additional ability to compensate for error.

In another embodiment (FIG. 13B), a needle insertion system 310 can be configured with structure to translate one or more of the ultrasound component 120 or the needle holder 306 perpendicularly relative to the pitch arm housing 310 to allow for the needle 130 to be actively centered by moving laterally on the target/vessel. To accomplish the additional degree-of-freedom, the addition of a lead screw (not shown) can be built into a pitch arm housing 310 perpendicular to an insertion lead screw.

In a further embodiment (not shown), a body mounted lead screw that translates the whole arm back and forth can be configured to provide additional degrees-of-freedom of movement of a needle. In other configurations, there can also be provided a stabilizing arm with joints that can be adjusted then held in place to hold the device for the user or a parallelogram arrangement of links that allow the whole arm to translate while being controlled at an arm-body interface. An additional amount of travel would be +/−5 mm. In various additional approaches, working from the goal of placing a needle, there can be provided a robotic arm having six degrees-of-freedom.

Figure 14A:
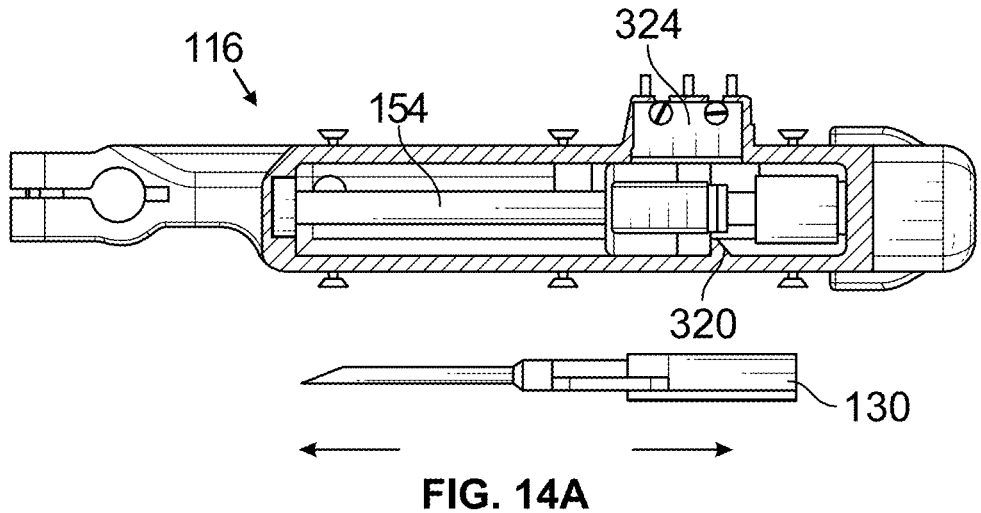
FIGS. 14A-B are partial cutaway views, depicting details of components of the vascular access device.
Figure 14B:
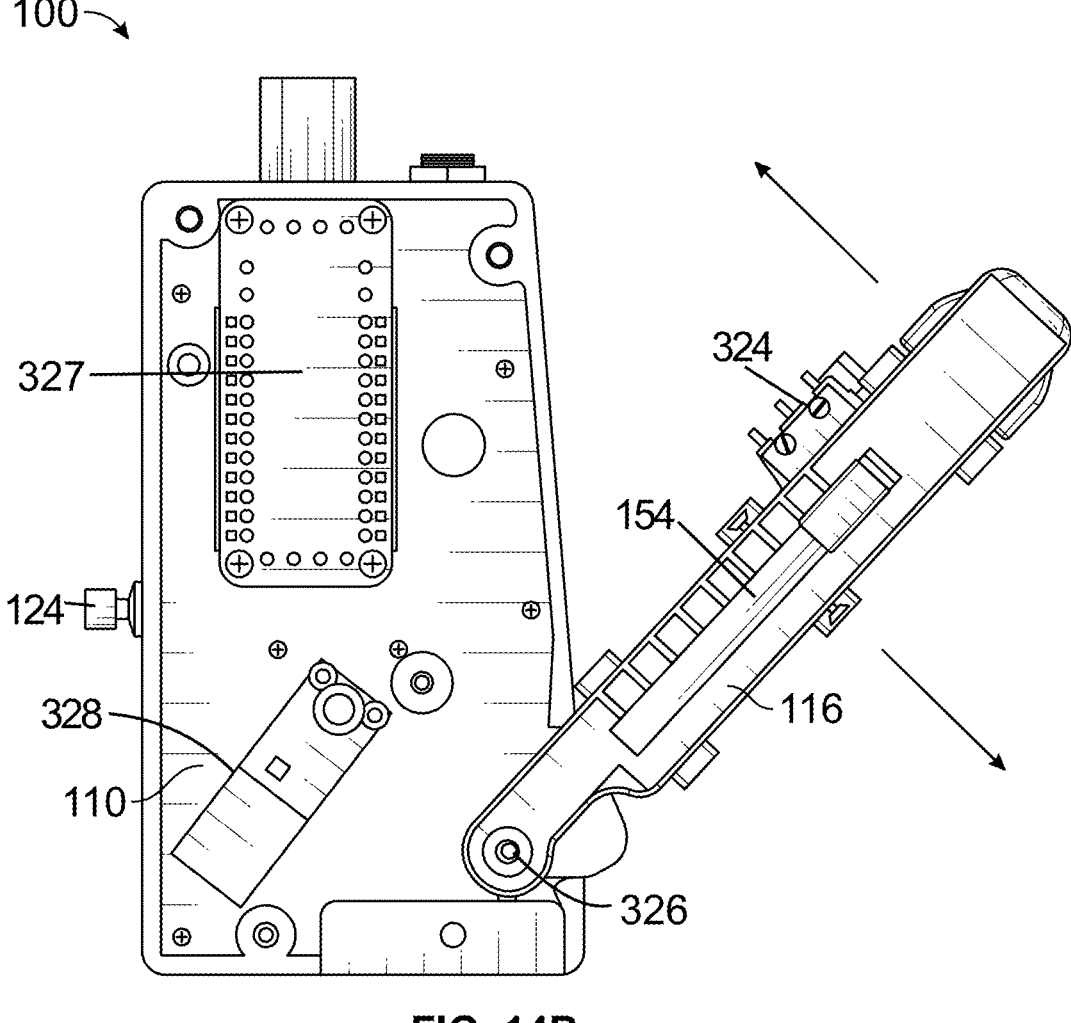

With reference to FIGS. 14A-B, further details concerning system degrees-of-freedom for a system 100 are now presented. The first degree-of-freedom is linear translation of the needle 130 along the pivoting arm 116 via motion provided by the lead screw 154 (FIG. 14A). The second is the pitch of the pivoting arm 116 (FIG. 14B) which pivots about pitch pivot 326. Notably, the main printed circuit board 327 communicates to control certain actions including that of the pitch motor 328 which operates to determine the pitch of the pivoting arm 116. In addition to the general degree of freedom, each can be associated with a positive or negative direction as an input to the kinematic model. For example, a linear translation toward target tissue can be considered to be a positive direction and a down pitch can be considered to be a positive direction, whereas a linear translation away from tissue can be considered a negative direction and an up pitch can be considered a negative direction.

In various alternative embodiments, the system can be equipped with structure creating small oscillations (i.e. dithering motion) during insertion motion. The same can reduce friction associated in moving components of the system into or about tissue. For example, system motors can be dithered during insertion to intentionally create small back and forth movements during the insertion motion to introduce vibration that can reduce friction and lower penetration forces.

A next level of input for the needle insertion system can involve the creation of a kinematic model which can include detailed geometric information of the needle insertion system. Such detailed dimensions of both the lengths of system components as they relate to the degrees of freedom, as well as the location of the joints as they can contribute to modeling the needle path of the device. In one embodiment, a 25 mm length needle is used in a kinematic model as it is the most typically used in placement for fistula. The kinematic model can be updated with other needle lengths when required. Needle offset from the linear motion portion of the arm is also known, for example with a needle offset to the start of that length (23 mm) and an overall offset to a needle axis (21.5 mm).

Figure 15:
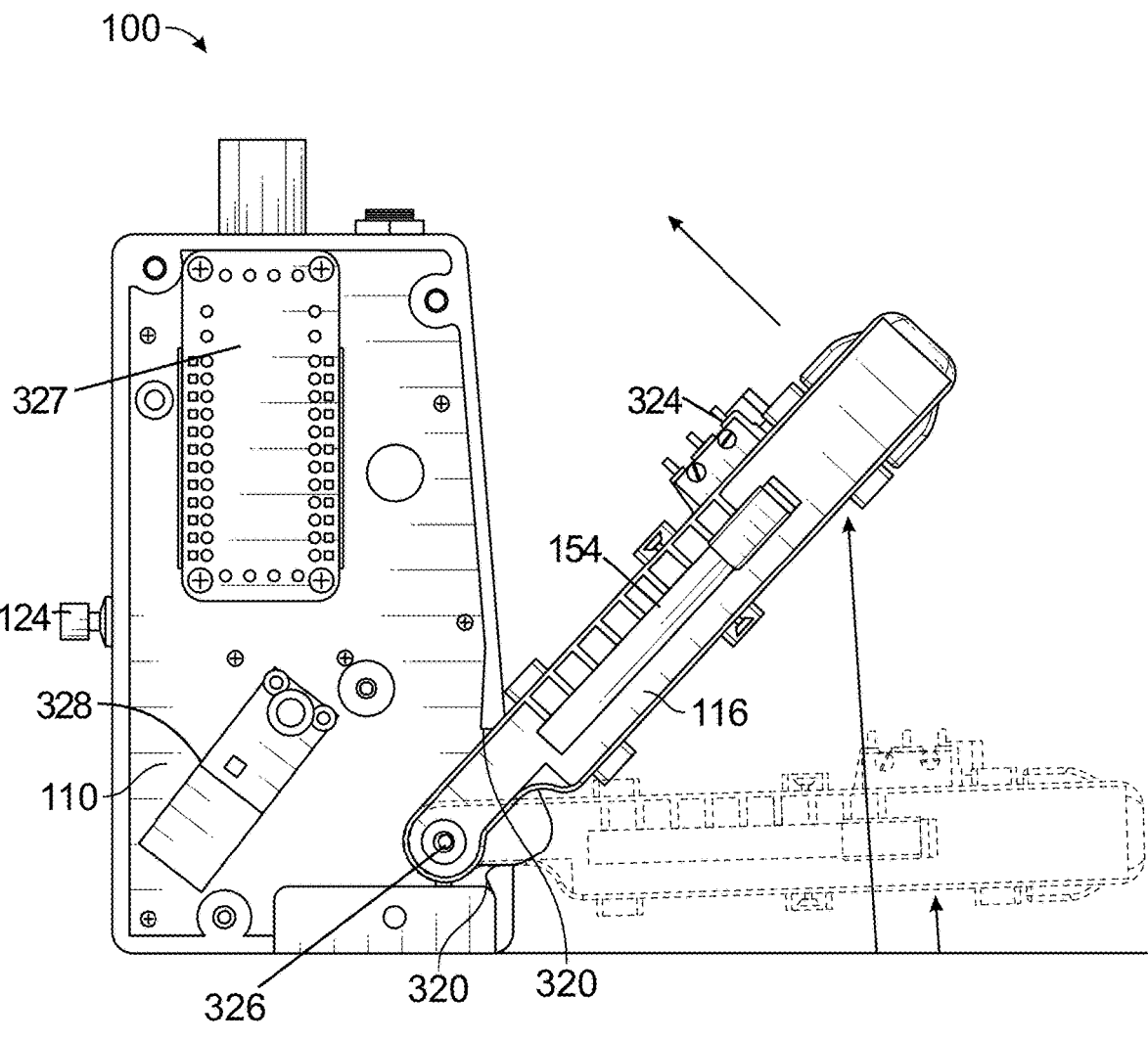
FIG. 15 is a partial cutaway view, depicting movement of a pivoting arm of a vascular access device.

Referring additionally to FIG. 15, with the lengths and joint locations of components of the needle insertion system known, hard stops 320 and range of motion are provided to make sure the system can be controlled as desired within mechanical limits. In one approach, the range of motion for pivoting is between 2.5 degrees and 47.5 degrees, with hard stops on both ends. As to the linear travel on the pivot arm, the range is 0-35 mm, with hard stops 320 1 mm or so further (See also FIG. 14A). Additionally, on the arm there is a home position limit switch 324 providing information concerning when the device is in a home or start position. The limit switch 324 could be mechanical as shown, or optical, or magnetic, or the switch could be omitted in favor of a motor current/torque homing algorithm.

With all the inputs from the physical system, a kinematic model is created to know the location of the needle tip with known inputs of pitch angle and linear travel. In order to track the location so the needle insertion system knows where the needle tip is, encoders (not shown) can be used on the motions so that locations can be returned to the control system. In addition, the properties of the motors controlling the motion will also be known in the control system, though not specifically required for the kinematic model. There can be many options for encoders and motors and a wide range of embodiments could be constructed.

In one or more embodiments, the needle insertion device can include a drivetrain including pitch and insertion controls. To control pitch, an encoder can be provided and can have a resolution of 0.01 degree/tick and can be embodied in an absolute encoder having a 12 bit ADC (360 degree) on motor gearbox output shaft and an 8.75:1 geartrain between a gearbox output shaft and a pivot shaft. The drivetrain associated with pitch can have a rated torque/speed of 243 N-mm at a joint and a 40.5 degree/sec speed at rated torque values. A max torque/speed can be 810 N-mm stall torque at a joint and 46.6 degree/sec motor at a no load speed. To control insertion, an encoder can be provided and can have a resolution of 0.029 mm/tick and embody an incremental encoder having a 0.2 mm nut travel per motor gearbox revolution and 7 encoder ticks per motor revolution. The insertion drivetrain can further have a rated torque/speed of 4.43 N rated force at nut and 41.7 mm/sec at rated force. A max torque/speed can include a 19 N stall force at nut and a 53.3 mm/sec motor no load speed.

In order to complete the full control loop, with the understanding of the geometry and kinematics of the system, combined with the knowledge of the locations/positions of these degrees of freedom, a next step is the assessment of where the target is located. In the current embodiment, the location is assessed or sensed by way of an ultrasound image. From the ultrasound image, the vessel/fistula will be identified in terms of depth and location. Once the user has followed prompts to align and hold the vascular access device in place, the user then triggers the system. Consequently, the targeting control loop of the vascular access system will create the desired needle path to accomplish vessel placement.

Figure 16:
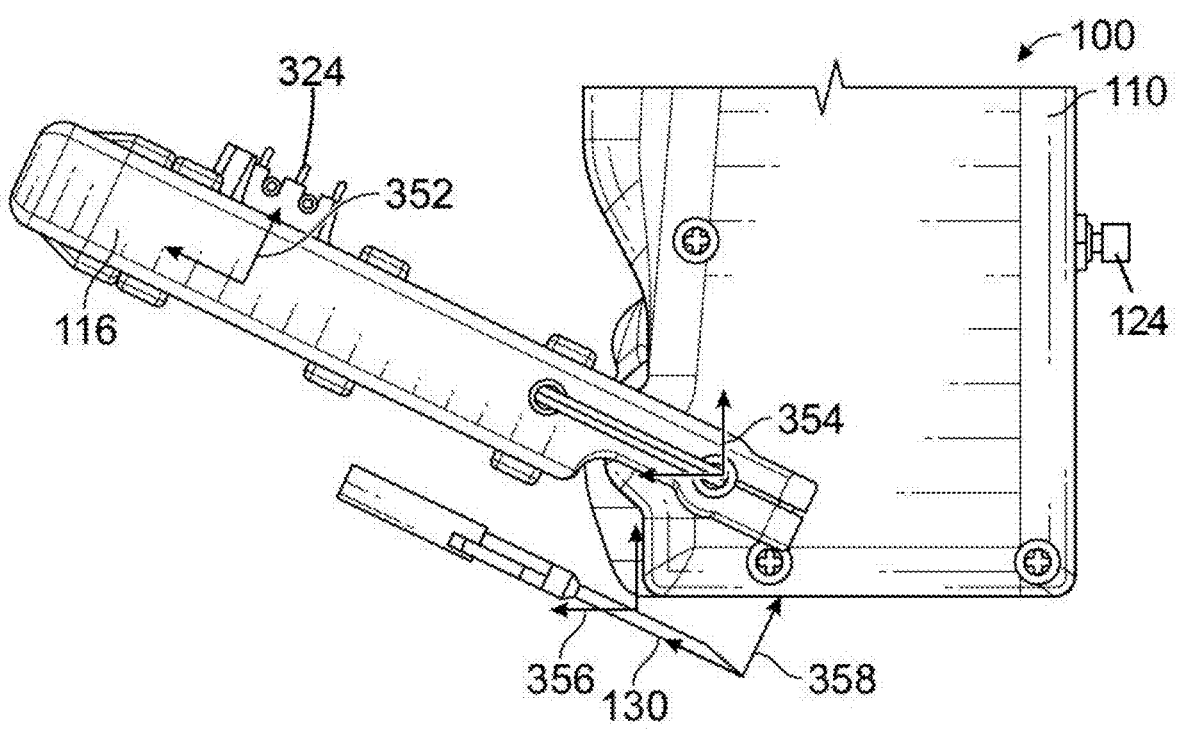
FIG. 16 is a side view, depicting reference frames of components of the vascular access device.

Turning to FIG. 16, there are shown the reference frames for the current vascular access system 100. In particular, there are four coordinate reference frames, an insertion coordinate reference frame 352, a pitch reference frame 354, an image or ultrasound coordinate reference frame 356 and a needle tip coordinate reference frame 358. With each coordinate reference frame defined, the system 100 can be set up to transform coordinates from one frame to another. Particularly taking tracking or targeting information from the ultrasound image and transforming it to the needle tip location.

Figure 17:
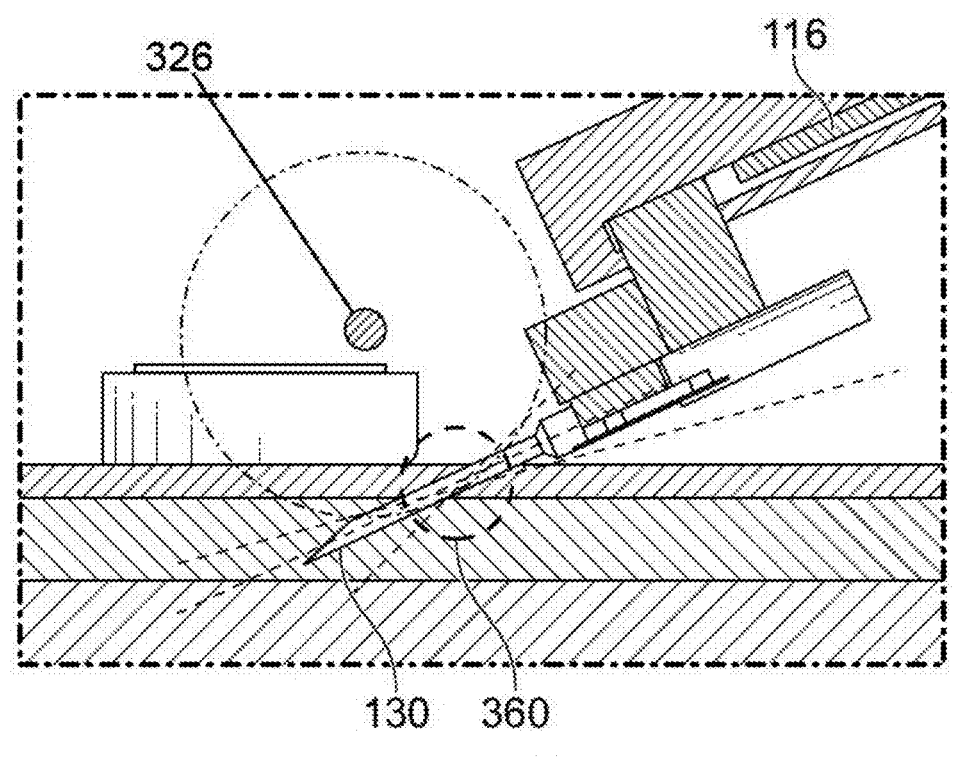
FIG. 17 is a side view, depicting details concerning operation of the vascular access device.

With reference to FIG. 17 which depicts an interpretation of needle trajectories across ranges of pitch angles, one advantage for needle delivery is to simplify the degrees of freedom to reduce mechanical and overall device complexity. This can be accomplished by selection of a pivot point range (360; circle) that while not fixed, but only moves an acceptable amount as represented by the dashed angled lines 361. This then relies on the skin/tissue around the entry to be flexible and accommodating of the change through the range of motion. Based on investigation and experience this tradeoff is one that can be made.

Figure 18:
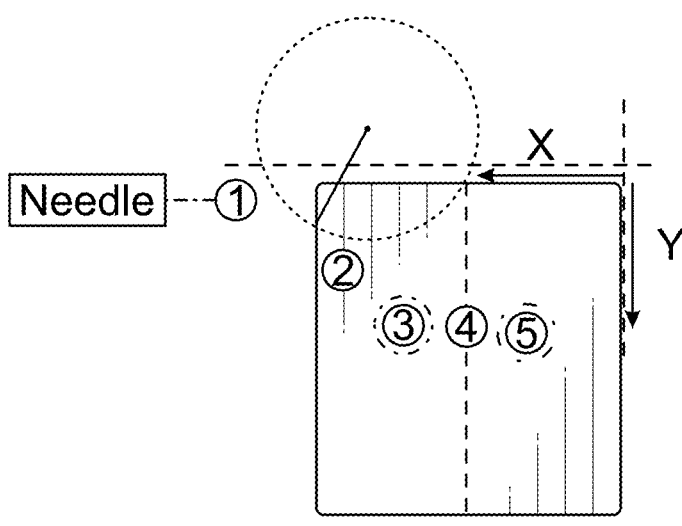
FIG. 18 is a schematic, depicting a longitudinal ultrasound image that shows a needle which pivots along an arc.

Further, with reference to FIG. 18, there is shown a schematic of a longitudinal ultrasound image that shows a needle which pivots along an arc shown as a dashed circle. Additionally, the needle can translate in/out along a straight line that is tangent to the circle. With the detailed geometry of the vascular access system known and through use of the mathematical model determining where the needle tip is located with the inputs from the two degrees of freedom, the vascular access system will use waypoints (1-5) to generate the path for the needle to travel. Each waypoint (1-5) gives the vascular access system discrete points to confirm it is performing as required to thereby ensure a point of the needle is delivered successfully to the target vessel. Waypoints 1-2 set the insertion angle of approximately 45 degrees in this example. Waypoints 3-5 translate the needle tip within the fistula/graft (not shown) in order to bury the needle tip further into the access for a more reliable placement.

Figure 19A:
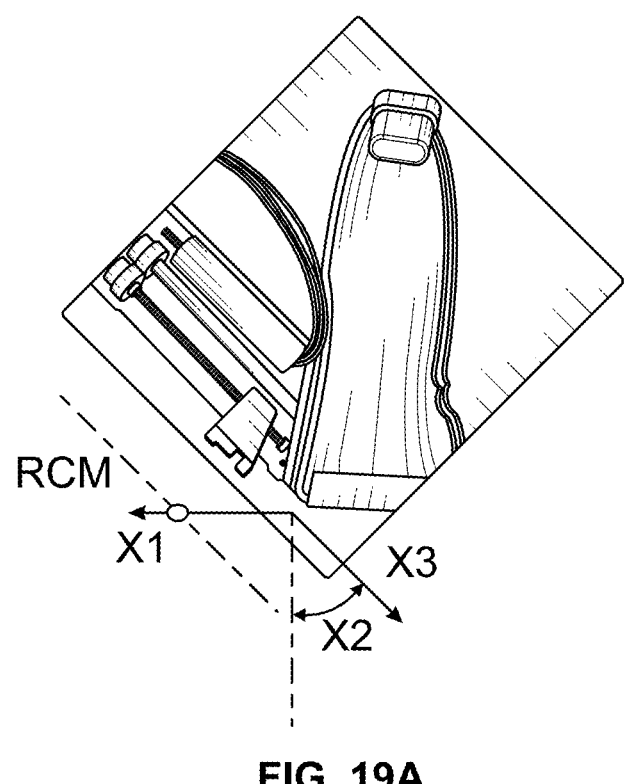
FIGS. 19A-B is an enlarged view and a schematic, depicting a cannulation approach involving a remote center of motion.
Figure 19B:
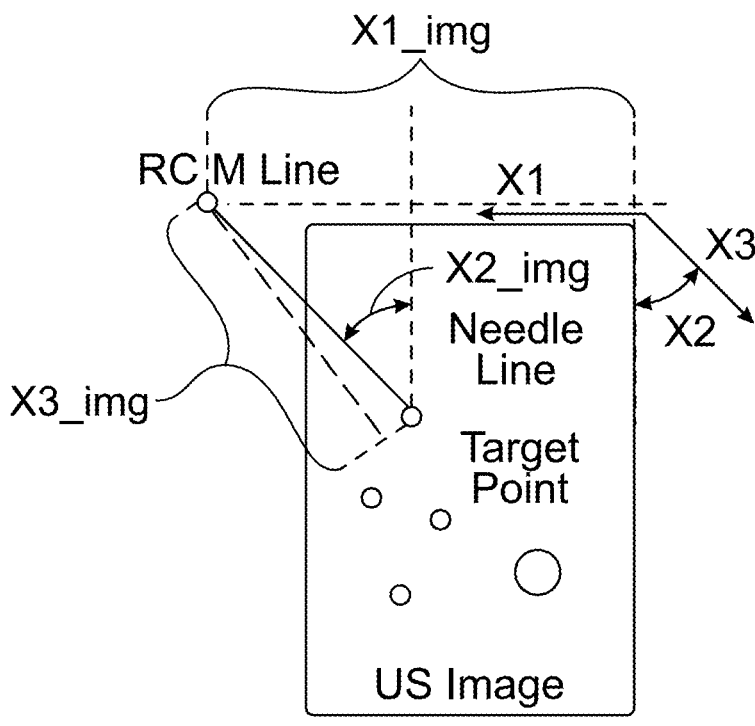

Overall, this disclosure has been focused on a vascular access device having two degrees of freedom, resulting in a pivot angle and displacement of a needle along a pivoting arm. In another embodiment as outlined in FIGS. 19A-B, there is presented an approach involving a remote center of motion (RCM). Such a device can embody hardware such that a needle has a virtual pivot point at a site of insertion on the skin. Thus, the vascular access system can virtually pivot around a specific location. This location could be the surface of the patient's skin, the vessel wall, or somewhere in-between. This eliminates the need for complex transformations and streamlines the computation required to take a target from an ultrasound image and transform it to the needle tip location.

With reference to FIGS. 20A-M, another embodiment to a vascular access system 400 is presented. This system 400 can embody one or more or all of the functionality and features described above. The vascular access system includes a body housing 410 containing the mechanical components to alter the pitch of a pivoting arm 416, an ultrasound transducer or probe or array 420, a needle holder assembly 460 that retains a needle 430, and internal control electronics for both motor control and activation and the transducer 420. In addition, connections to both power and a computer run though the body housing 410. FIGS. 20A-F show various side and perspective views of the vascular access system with the needle holder assembly 460 spaced from the housing 410. Contained within the pivoting arm 416 is an insertion motor 417 that is configured to drive a needle 430.

Figure 20G:
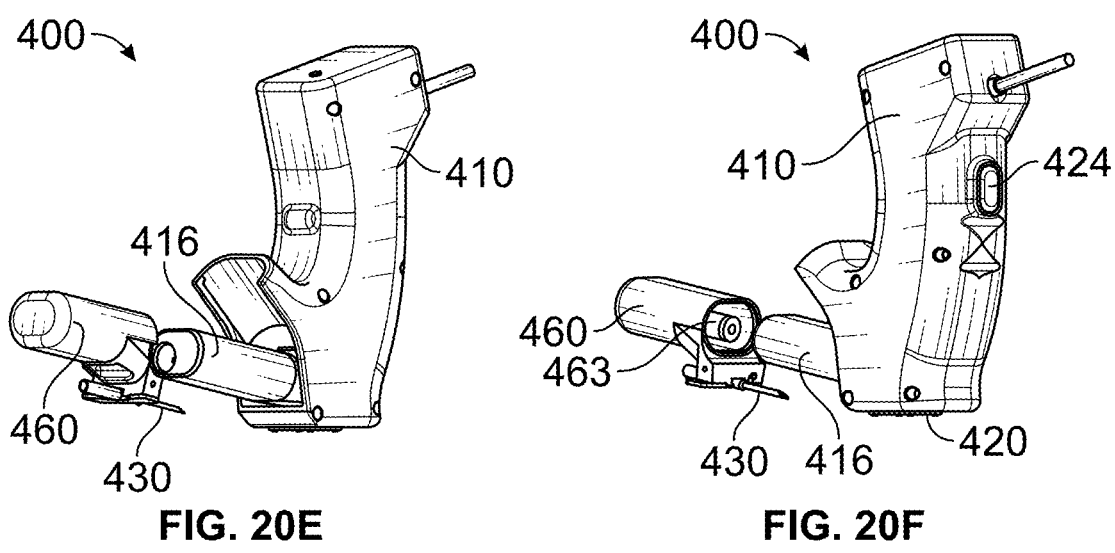
Figure 20G:
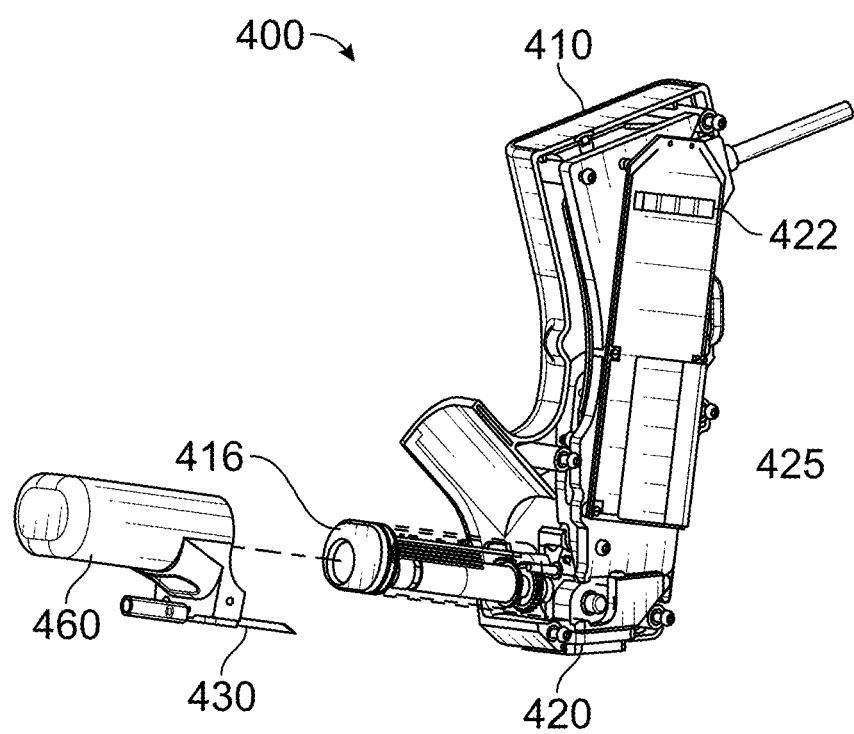
Figure 20H:
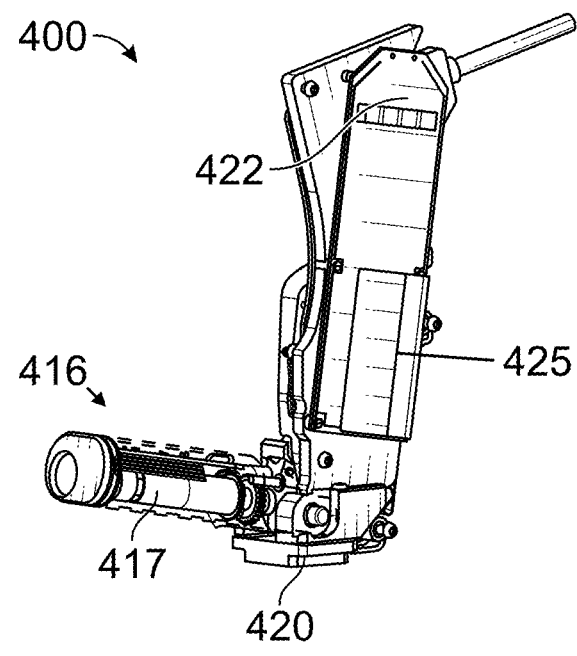
Figure 20I:
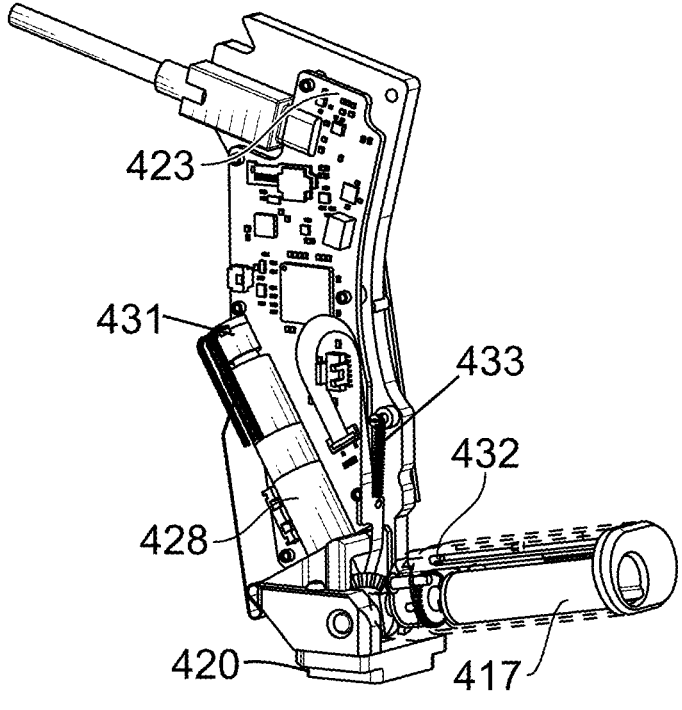

FIGS. 20G-I highlights certain of the internal components of the body 410 and the ultrasound array or transducer 420, with shell components of the body housing 410 removed. It is to be noted that a custom integrated transducer 420 is incorporated into the design. Moreover, there is provided an ultrasound circuit board 422 associated with the array 420, and a controller board 423 that controls the functioning of the system and moving components. Also shown is an ultrasound transducer flex circuit 425. An activation button 424 (See FIG. 20F) is configured to be in electronic communication with the controller 423 which communication through or with the flex circuit 425 and ultrasound circuit board 422. Further, a pitch motor encoder 431 is associated with the controller 423 and a pitch motor 428 to facilitate controlling pitch of the pivoting arm 416. Also shown is a spring 433 that engages and tensions the flex circuit 477 (see FIG. 20M) throughout pitch range of motion.

Figure 20J:
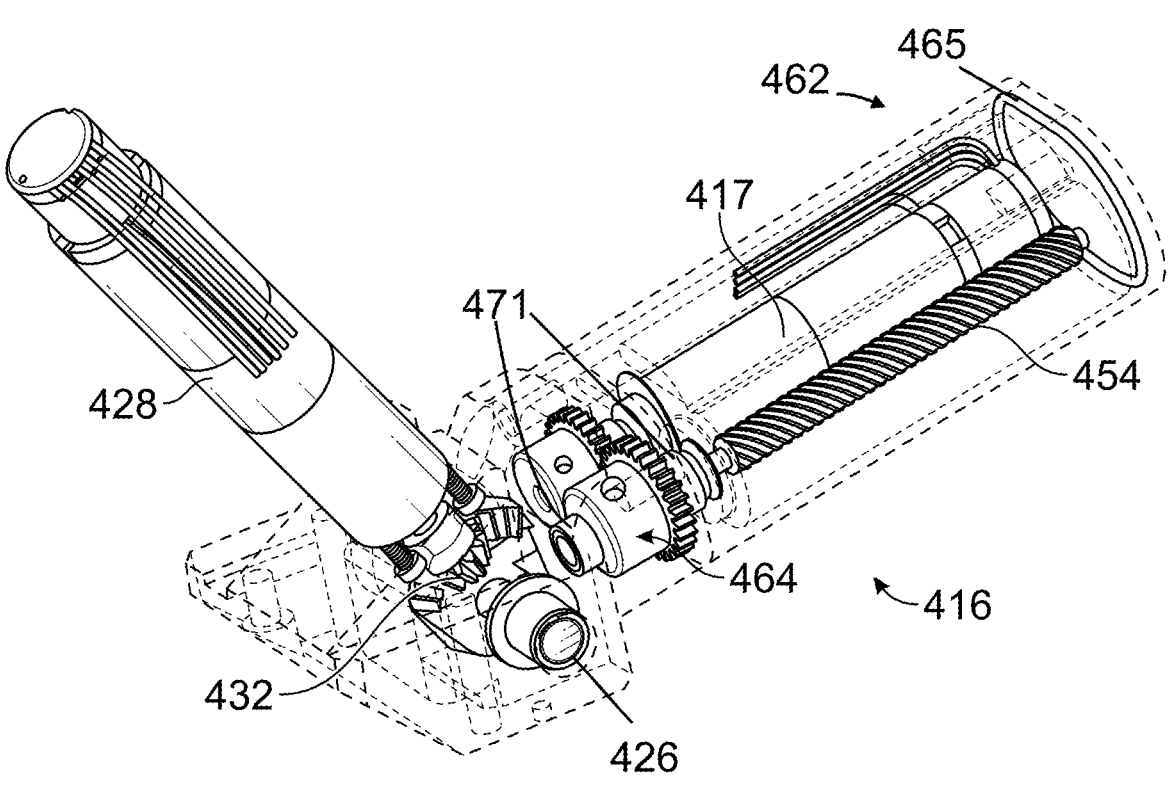
Figure 20K:
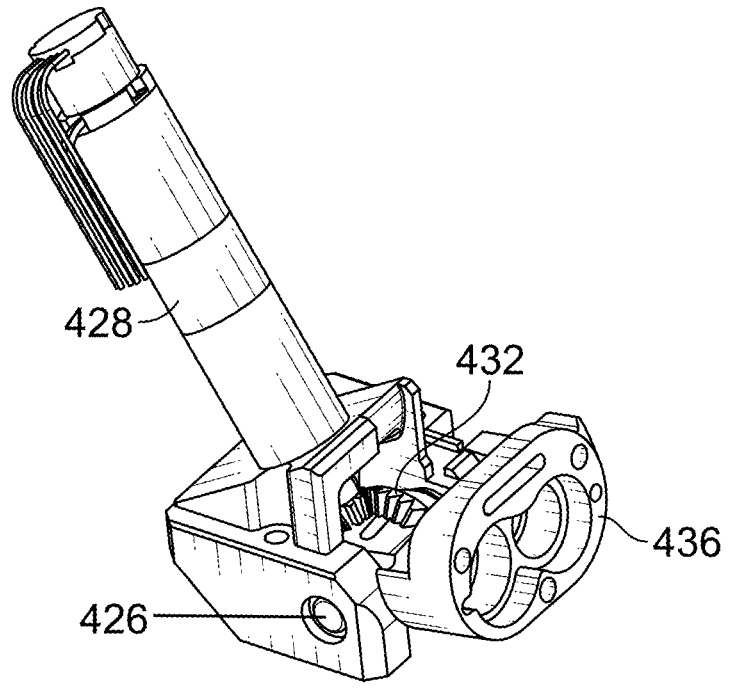
Figure 20L:
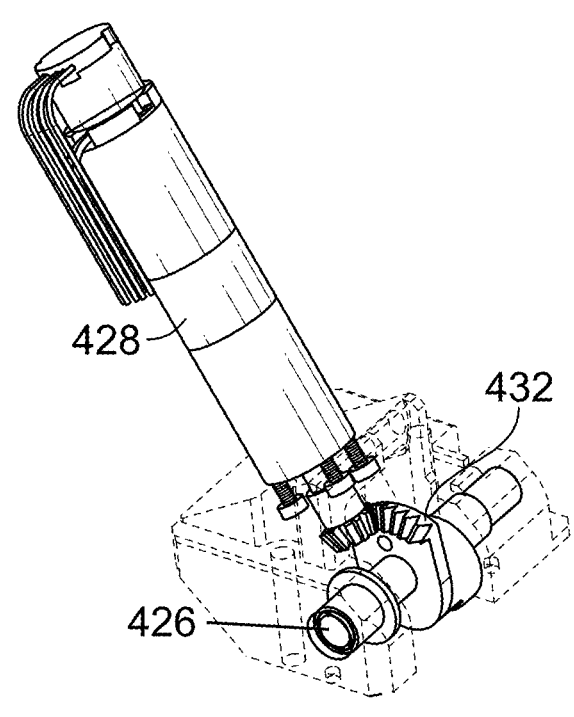

Mechanically and electronically connected to the body 410 is the pivoting arm 416 (See also FIG. 20J-L). Through a geared transmission, the angle of the arm 416 can be changed about a pivot 426 via an electric motor 428 mounted within the body. Aligning with the traditional guidance for needles entering the AV fistula for hemodialysis, the angle of the arm 416 can range from about 0 (parallel to the bottom of the body) or from about 10 to 46 or more degrees, with likely range for use in the 15 to 45 degrees range. In addition to the pitch control, the pivoting arm 416 has a needle mounting 462 assembly and a needle drive system 464 (best seen in FIG. 20J). The needle mounting assembly 462 is configured to receive the needle holder assembly 460 (FIG. 20G) where sealing is provided by an O-ring 465 or the like.

In one embodiment, the ultrasound array 420 of the system 400 is rigidly attached or mounted at the bottom of the housing 410. The integrated ultrasound array 420 allows for more refined packaging and better integration of the ultrasound output with the needle application system.

As before, a laptop or other computer (not shown) can be provided as part of the system. For this embodiment, the current programming and control can be from a USB cable attached laptop. A non-USB cable such as EtherCAT can be used as an alternative, the same facilitating enabling real-time/deterministic communication. Here also, in addition to being able to work with the ultrasound images coming to the computer from the ultrasound array, the laptop allows for flexibility in programming and refining the movements of the system 400. In an alternative embodiment, the system 400 could still be attached to a laptop with a fully developed user-interface to allow the laptop/cart to accomplish computational or control work. In yet another embodiment, all the system work can be connected with the electronics within the handheld device requiring only a power connection (or even battery power) to operate. In one aspect, there can be a full integration of processing (computer) function into the device itself. As with the previously disclosed embodiment, this system 400 distills the design to minimal degrees of freedom so that the system 400 can perform as desired in all conditions of use.

Again, the degrees of freedom present in this embodiment are pitch and insertion. Pitch rotates the needle to a desired insertion angle. Additionally, as the needle advances pitch can be used to alter the needle path angle forward along the target vessel. The combination of these two degrees of freedom allows the system to advance the needle into the target fistula or graft and then adjust to allow the needle to pass down the fistula or graft, safely, for complete insertion.

In the disclosed embodiment, a range of motion is about 10 degrees to 46 degrees with the lower angles for final insertion, such as approximately 15 degrees. Still referencing FIGS. 20J-L, the motor 428 is used to drive a bevel or pitch gear 432 and control the angle of pitch. A proximal end of the pivoting arm 416 is configured to engage the pitch gear 432 so that as the pitch gear 432 is caused to rotate, the arm 416 pivots relative to the body housing 410 and relative to target tissue. FIG. 20K depicts a connector 436 with the rest of the pivoting arm removed and FIG. 20L shows the connector also removed.

The angle of the needle 430 for insertion needs to be sensed for the control circuit. Various approaches can be taken, such as the same being provided by a motor encoder, with a homing step, or an absolute encoder could be used in the device body or arm to measure without a required homing step.

Insertion of a needle 430 within target tissue involves the linear advancement of the needle 430 to the target location. This can be along the angle created/controlled by the pitch. Insertion consists of linear motion to insert the needle 430 into a patient along path to target vessel or location. The needle 430 starts outside of patient and is advanced through skin layer, into vessel/target (not shown). In one embodiment, up to 35 mm of travel is provided. Length of travel is selected to ensure the needle 430 can be held away from the patient to minimize the likelihood of inadvertent needle sticks but close enough to make the insertion fast once the user decides to insert. Here also, the needle can be protected (i.e. sheathed or covered) until it is needed. In an alternative embodiment (not shown), the needle protective structure can be removed by the system itself (rather than the user) as part of a delivery process.

As best seen in FIG. 20J, the pivoting arm assembly 416 includes a motor 462 that is connected to a leadscrew 454 to drive and translate a needle holding assembly 460 toward and away from a target. Notably there are two spaced radial bearings 471 configured to allow the leadscrew 454 to be cantilevered, which thus allows for the removal of the needle holder 460 for cleaning. The needle holding assembly 460 is removable for cleaning and is designed to present smooth, wipeable surfaces. In this way, the assembly is easier to clean and simplifies and eases user workflow. In one alternative embodiment, the needle holding assembly 460 can be equipped with magnetic encoder technology that involves a magnet configured within the assembly that communicates or cooperates with one or more sensors integrated into the system arm to thereby provide information regarding needle holder presence and/or absolute positioning.

Figure 20M:
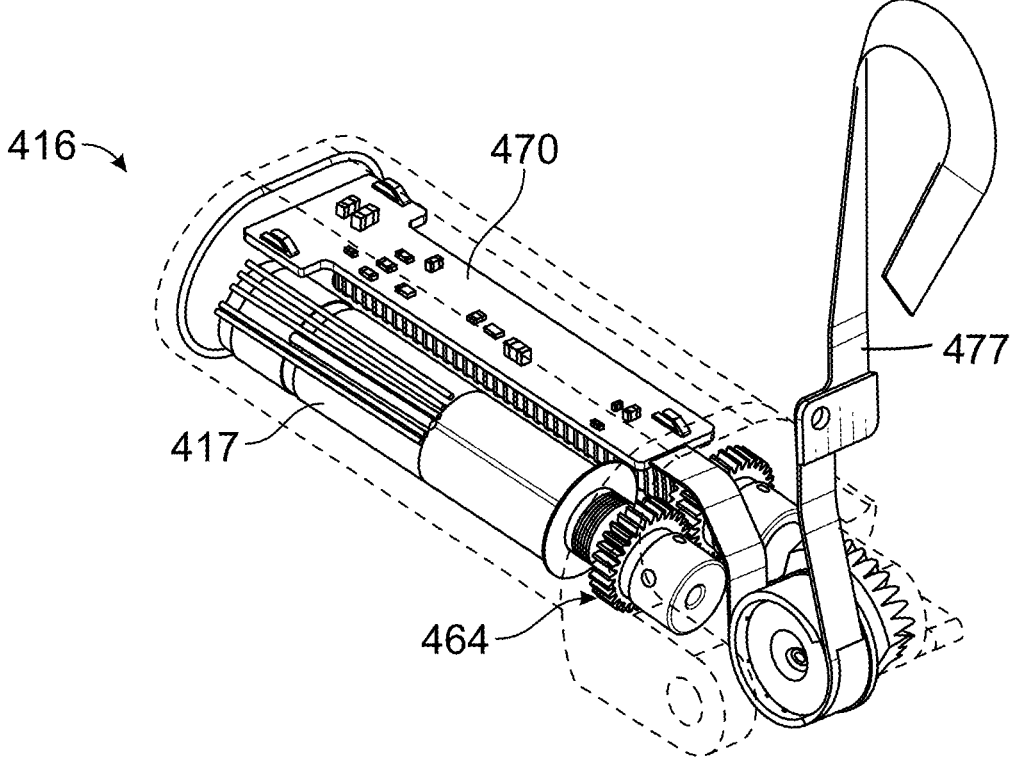
Figure 21A:
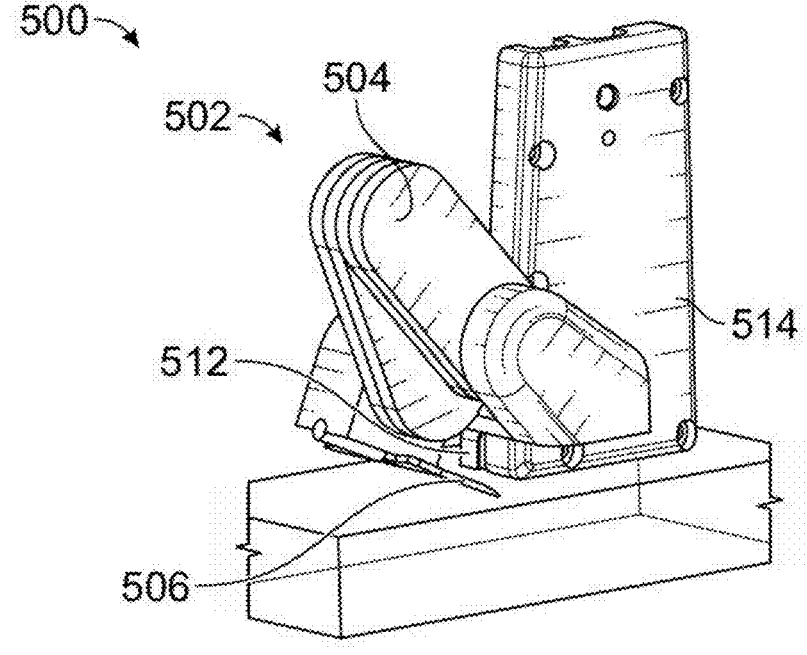
Figures 22A, 22B, 22C:
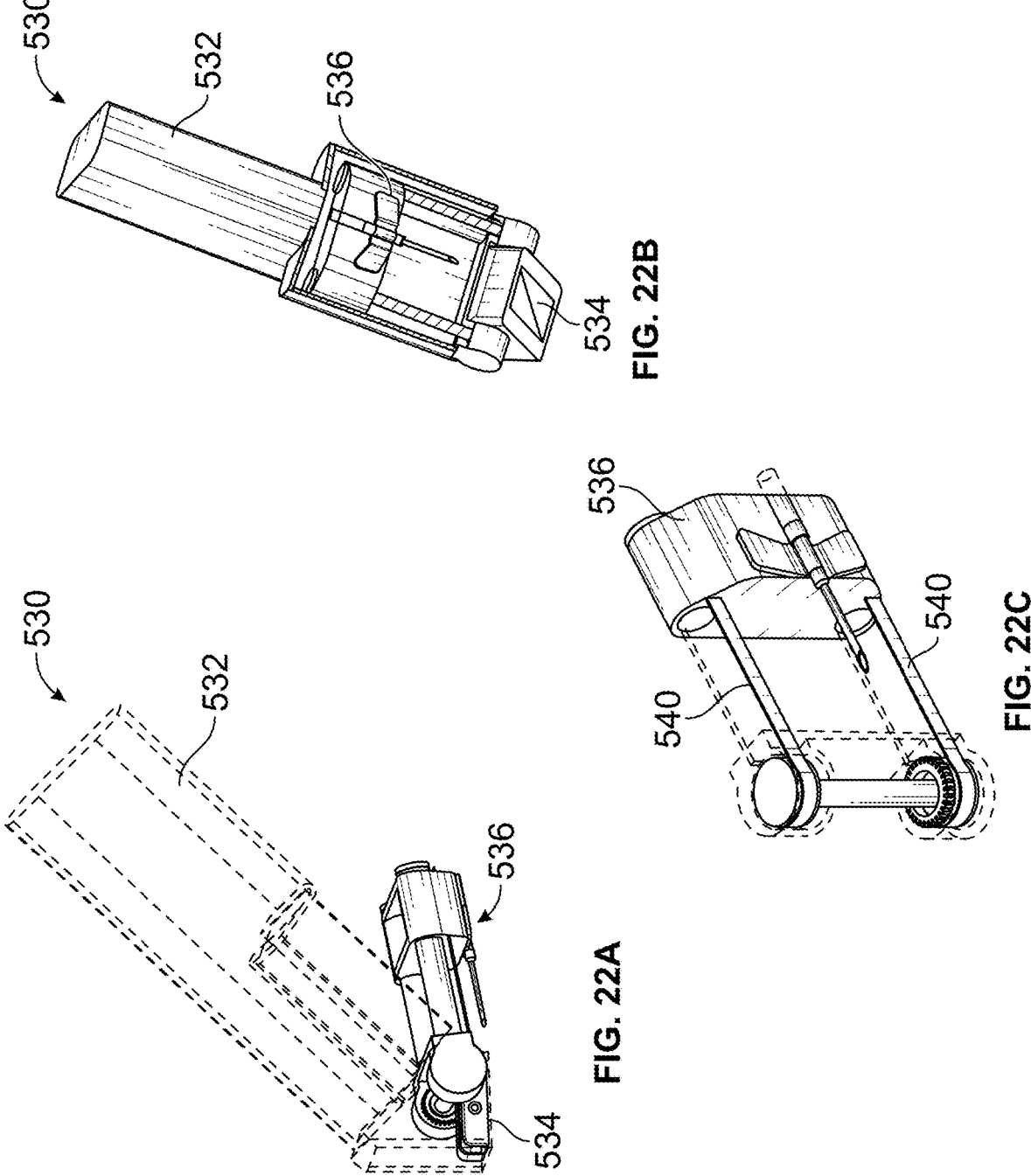
FIGS. 22A-C are various views, depicting portions of another embodiment of a vascular access device.

With additional reference to FIG. 20F, the needle assembly 460 includes a leadscrew receiving structure 463 that receives and engages with the leadscrew 454. As shown, the motor 462 driving the lead screw 454 is located in the arm 416, and the needle drive system 464 is employed to transmit rotating energy from the motor 462 to the leadscrew 454. The leadscrew 454 and leadscrew receiving structure 463 thus cooperate to position the needle assembly 460 as desired relative to patient anatomy. Through the connection of the leadscrew 454 and leadscrew receiving structure 463 of the needle holder assembly 460, rotating the leadscrew 454 results in translating the needle holder assembly 460 as desired relative to target tissue. As shown in FIG. 20M, the pivoting arm assembly 416 additionally includes electronics 470 that cooperate and communicate with the controller 423 via flex circuit 477 to control operation of the arm 416.

In another embodiment, an inductive position sensor can be employed. With this approach, a simple piece of metal is used in the needle holder rather than a magnet, and a series of coils (similar to antennas) are embedded in the arm circuit board rather than discrete chips to sense a magnet. Further, with this approach inductive sensing is more resistant to EM noise generated when motors are active and a range of the inductive position sensor is smaller so the metal for inductive position sensing must be placed closer to the arm circuit board than a magnet would have to be.

Turning now to FIGS. 21A-23B, there are presented additional embodiments of vascular access devices and systems. These embodiments can embody one or more of the various features and functionality associated with the approaches described above. As shown in FIG. 21A-E, one such additional approach to a vascular access system 500 embodies a parallelogram mechanical constraint arrangement 502 to effectuate controlled movement of a pivoting arm assembly 504. In this way, a remote center of motion joint design is provided which minimizes movement of a needle 506 at a given location 507. Here, the location of the remote center of motion is fixed by the system 500 design. FIGS. 21B-C show the movement of the needle 506 attached to a needle holder assembly 508 relative to an insertion site and FIGS. 21D-E show the insertion of the needle 506 within a target vessel 510. An ultrasound transducer or probe or array 512 affixed to a housing or body 514, or integrated therein (FIG. 21A), provides information to guide the needle 506 into and within the target vessel 510. Various motors (not shown) and associated electronics (not shown) are provided in one or more of the pivoting arm assembly 504 or system body or housing 514 to move components of the system relative to the target vessel 510. Notably, further structure and functionality can be added to this system 500 to provide additional degrees of freedom such as pivot functionality configured at a base of the system 500 to allow the system 500 to perform additional angular alignment to the target vessel 510.

In another embodiment (FIGS. 22A-C), an access system 530 can embody a housing or handle 532 having a conveniently designed grip design. Attached to a distal end or base of the handle 532 is an ultrasound transducer or probe or array 534. The pivoting of a needle holder assembly 536 relative to the handle 532 can be accomplished in one or more of the manners described above. Thus, motors (not shown) can be configured within the handle 532 as moving mass away from moving joints improves response and is more ergonomic. A motor (not shown) in combination with a transmission can be employed to route power to one or more moving joints at a given time. In one approach, steel or similar bands 540 can be configured to pull the needle holder assembly 536 away from the base of the handle 532.

Figure 23A:
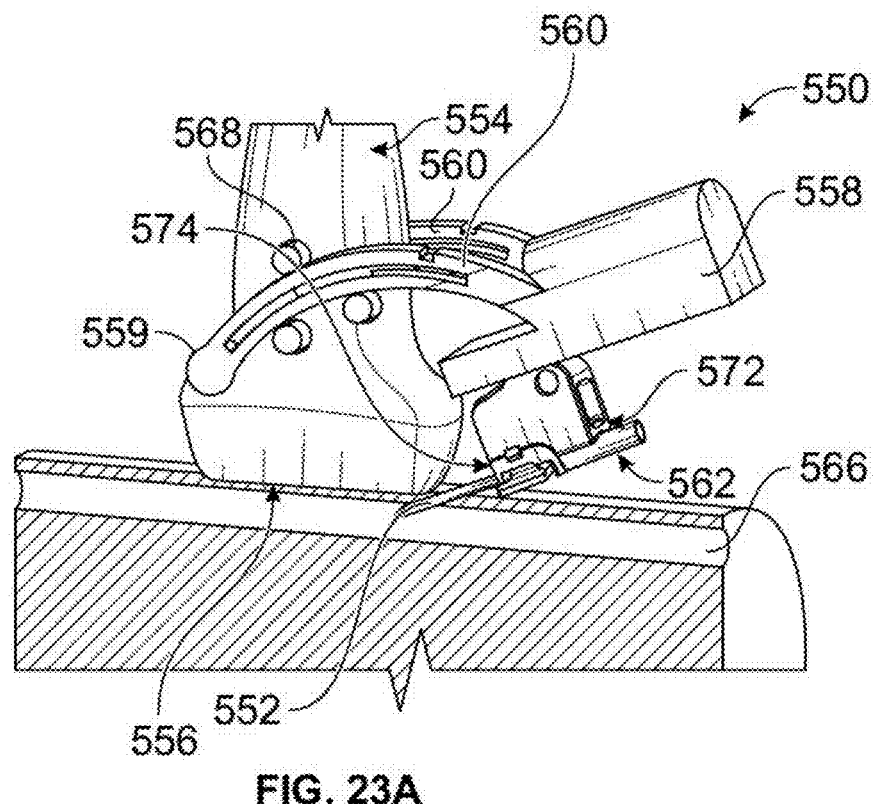
FIGS. 23A-B are perspective views, depicting another embodiment of a vascular access device.
Figure 23B:
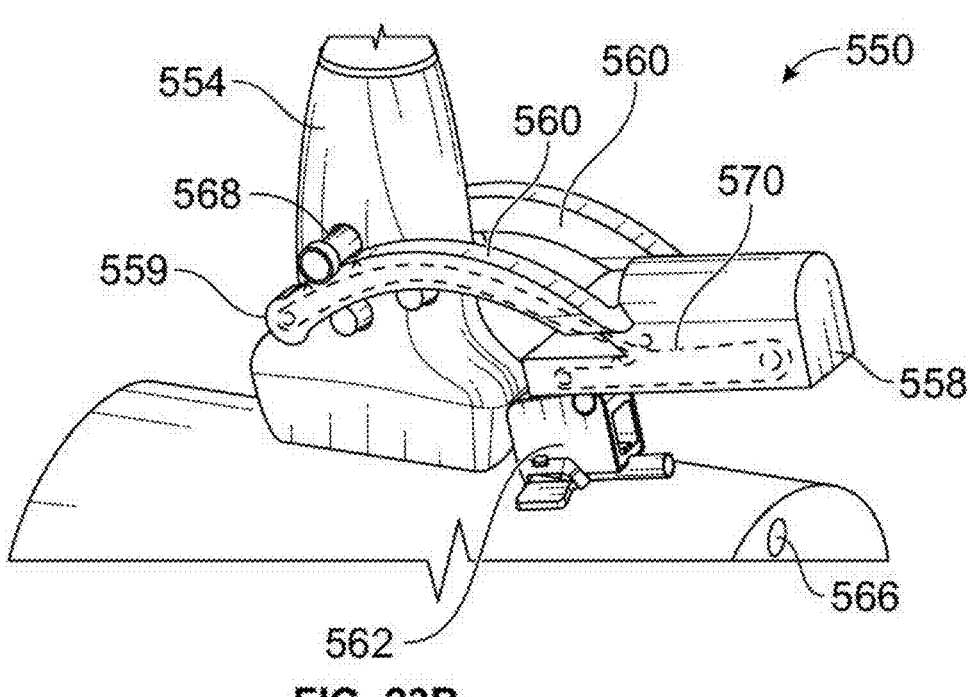

With reference to FIGS. 23A-B, a spherical remote center of motion access system 550 is presented. Here also, the remote center of motion joint design minimizes movement of a needle 552 at a given target location. The system 550 includes a housing 554 having a general shape of an ultrasound transducer assembly but with processing done remotely such as on a cart (not shown) positioned alongside of the patient's treatment chair. The transducer or probe or array 556 is arranged at a distal end or base of the housing 554. A pivoting arm 558 houses an insertion motor (not shown) and includes a pair of spaced, arcuate arms 560 configured to engage opposite sides of the housing 554 and to translate with respect to the housing 554. Terminal ends of the arcuate arms can be provided with a counterweight 559 to balance the device during pitch movement. Motors (not shown) are additionally provided to accomplish the movement of the arms 560 relative to the housing 554 and to translate a needle holder assembly 562 relative to a target vessel 566. A motorized pitch axis 568 provides a virtual pivot (such as up to or more than 3 mm) below the surface of the skin. As shown in FIG. 23B, a cable 570 can be provided and routed to drive insertion along a desired axis. Moreover, the needle holder assembly 562 can include one or more of a flash detector 572 and an electromagnet 574 for needle drop.

Turning now to FIGS. 24A-E, there are presented details concerning ultrasound transducer or probe or array arrangements that can be embodied in one or more of the vascular access systems disclosed herein. Notably, Doppler is a technique that allows the ultrasound subsystem to determine the velocity of particles within its plane of view. It cannot measure velocity that is perpendicular, so by tilting the array to an angle of approx. 15 to 45 degrees the motion of particles (i.e., blood) can begin to be detected. This facilitates assessing blood flow velocity, volumetric blood flow rate, pulsatility (change in blood flow rate throughout heartbeat, correlated to outflow stenosis), and flow direction. Further, a tilted array enabling doppler can be utilized for assessing the access and identifying any issues with the patient's access early as mentioned above. Additionally, doppler allows the device to measure flow direction. It can be important for the dialysis treatment that the needle returning clean blood to the patient is facing with the flow of blood (towards the heart). Doppler allows for the confirmation that the device is facing the correct direction before a needle is placed. This can be particularly useful in "loop grafts" where the access makes a 180 turn inside the patient's arm.

With the use of an automated needle or catheter delivery system, the system uses a sensing system in place to understand the target anatomy and determine the path for the needle prior to placement. Conventionally, when placing cannulas for dialysis, the user relies on visual, tactile, and auditory feedback (i.e., "look, listen and feel") to make the assessment of where and how to insert the needle. While this feedback is still available to the user in order to make determinations in addition to automatic placement of the needle, additional sensing can be advantageous. Due to the complexity of many patients' fistula or target anatomy, ultrasound provides a significant increase in the information available and allows for the automatic system to determine needle path and monitor its placement. Additionally, with a technology such as ultrasound, more than just imaging data maybe collected and tracked. Thus, an ultrasound array can provide the needed information to better automate needle delivery. It has been noted that while a single linear ultrasound array can be employed to image internal anatomy, it lacks an ability to facilitate linking what is imaged with targeting or sensing information for automated needle delivery. That is, in certain instances, there can exist a challenge with the introduction of slightly off axis angles where usable information available begins to drop off. In particular, when a single linear array is placed longitudinally with respect to a target vessel, the information available begins to drop off as the array presents a view that is not actually down a center of the target vessel and as a result, can lead to incorrect assessments by the automated system. Further, when placing a single linear array transverse to a target vessel, only a single cross-section of the vessel is provided, and while some assumptions can be made regarding how the target vessel or fistula changes along its length, it can be difficult to fully understand the path a needle or catheter must follow during placement.

Accordingly, to provide a more useful and complete imaging of target anatomy for automated needle or catheter insertion, a T-array, I-array, or a two parallel ultrasound transducer array arrangement can be employed in accordance with the invention. A long linear array ultrasound is made up of many transducer elements. This allows for system electronics controlling the ultrasound to control adjacent elements as a phased array and increases the imaging capability from the ultrasound probe. In one or more embodiments, an array of one hundred twenty-eight elements can be employed, and these elements can be split into two equal arrays of sixty-four elements. Such a configuration is beneficial to a vessel identification and targeting application as the arrays are separate but electrically connected and controlled.

In one embodiment (FIG. 24A), the ultrasound transducer, probe or array 600 includes a first array 602 that is oriented perpendicularly to a second array 604. The first array 602 is transverse to the vessel or fistula 610 and will clearly observe the cross section of the vessel 610, thereby allowing for assessment of size and location (depth). The second array 604 will provide longitudinal information for a portion of the length of the vessel or fistula 610. Combined together, the arrays 602, 602 provide more complete data for feedback so the user can position the system in alignment with the vessel or fistula 610 for needle or catheter 612 delivery based on signals from the system to the user to move the system a desired direction and/or distance.

Figure 24A:
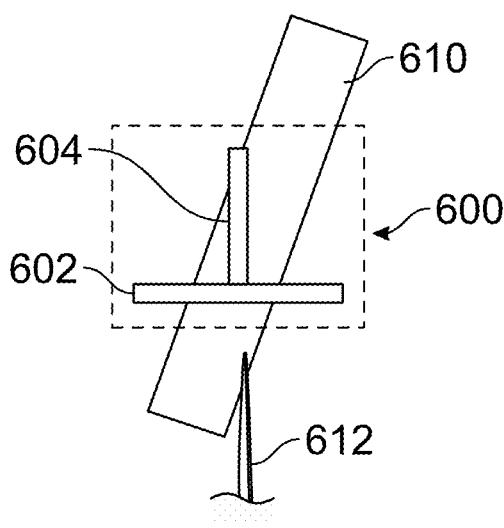
FIGS. 24A-E are schematic and perspective views, depicting configurations of ultrasound transducer or array or probe assemblies.
Figure 24B:
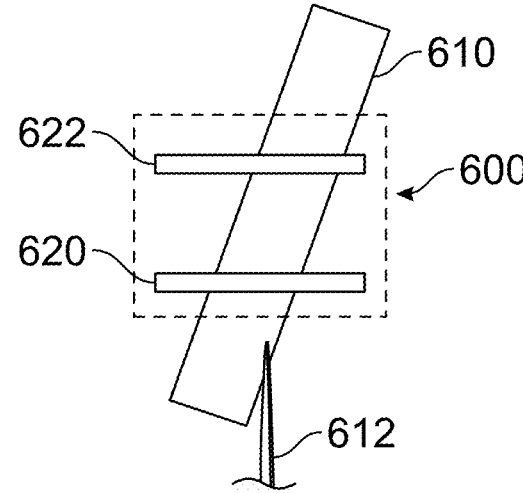
Figure 24C:
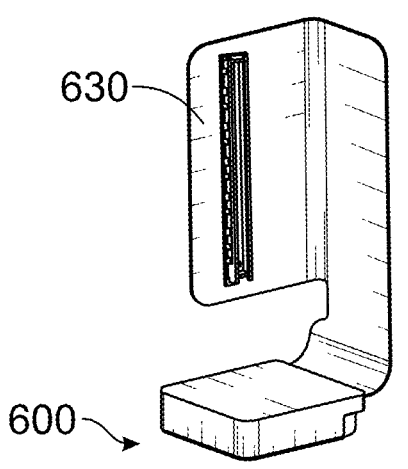
Figure 24D:
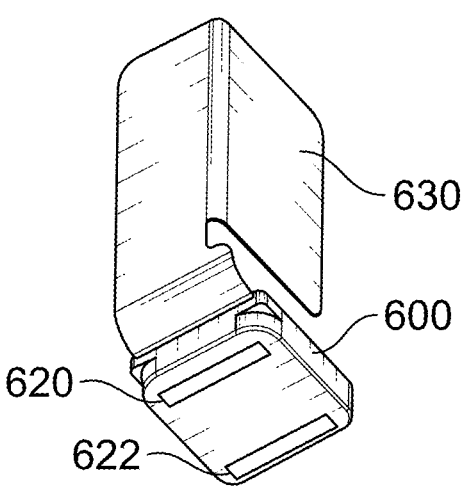
Figure 24E:
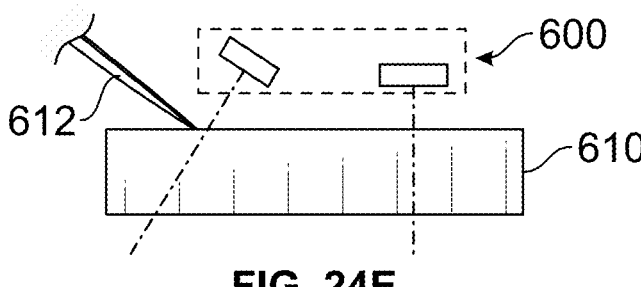

In another embodiment (FIG. 24B), two arrays 620, 622 are arranged parallel to one another and arranged transverse to the vessel or fistula 610. The resultant imaging presents two cross-sections of the vessel or fistula 610 at a known distance apart. This distance between arrays can be based on the length of the needle or catheter 612 to be inserted and the specific application. Additionally, distances between transducers can be informed by anatomic assumptions and the ability to infer the anatomy between the two images. In one particular aspect, a distance of 14 mm can be used, but can range from 1-3 cm or more depending on anatomy and application. The parallel transducer arrangement simplifies the process of aligning the transducers to the vessel since entire cross-section of the target vessel will be observable in each transverse view. With the cross-sectional image of the vessel present, the centerline of the vessel can be measured relative to the known device centerline. Additionally, with two parallel transducers at a known distance from each other the center points of each vessel cross-section can be utilized to determine directionality (angled left, right, up, down) of the vessel via interpolation, thus providing a means to ensure the device can be translationally aligned to the center of the vessel as well as rotationally aligned to any directional change of the vasculature that is present. Notably, there is an interaction between the first cross-section and the point of intersection with the needle/catheter 612 and the vessel or fistula 610 to facilitate proper device insertion and advancement. One such arrangement is depicted in FIGS. 24C-D, which show the array attached to a flex circuit 630 that communicates with a controller (not shown).

In alternative or additional embodiments, an ultrasound transducer, probe or array can embody one or more of a tilting primary array, an "I" shaped array, or an assembly configured to control the distance between the two transverse arrays. Array tilting can allow for a wider view of the needle entry to the vessel. Additionally, array tilt can allow for doppler assessment which increases the information from the ultrasound, especially in the case of wanting to track the quality and condition of the fistula over time (See FIG. 24E for example). Additionally, one or more embodiments can include an array element perpendicular to two parallel arrays to create an I-shape. The resulting imaging can be the two transverse views of the target anatomy at a fixed spacing as well as a short segment of longitudinal imaging. With alignment aided with the transverse images, a centered longitudinal image provides feedback as the needle progresses down the vessel.

Further, structure can be provided to accomplish spacing between two arrays with a lead screw or servo, manually or automatically in response to system data collection. The motion would maintain the parallel nature but could move the array to be suited to the application, such as a different needle or catheter length, or making an adjustment to review the presented anatomy.

In another particular aspect, the system can be configured to prompt the user to move the device in a set pattern over the target location. In doing so, imaging data can be collected to create a 3D model of the target vessel along with landmarks so that the system would know where it is prior to needle placement and compute the path for needle entry. Further, ultrasound in the system can be employed to scan along the length of the fistula or graft and provide identification of the patient, similar to a fingerprint, so that even without technician entry the system would know the patient and be able to bring up information about their treatment and treatment history.

In one embodiment, patient scanning is performed as needed such as on a periodic basis so that the position of the targeted vasculature or graft is confirmed. In one approach, additional scanning can be conducted on a schedule such as up to every six or more months. The pre-scanning process can involve medical personnel that develop a strategy and plan to map an approach to advancing one or more needles into targeted vasculature through an acceptable path. The strategy or plan can include a small range of acceptable paths as well as a most desired path to vascular access. This plan can include mapping paths to numerous pre-determined cannulation sights which can then be accessed on a rotating basis via a rope ladder access technique. The acceptable cannulation sights and paths can all be determined after the pre-scanning process and prior to the patient undergoing dialysis. Accordingly, in one embodiment, the cannulation site and path to cannulation does not need to be calculated in real time—but can be determined before the patient puts their arm under the system.

In one embodiment, a vascular access system includes structure and functionality to target vasculature and to position one or more needles or catheters within the target vasculature without the need for skilled personnel. In one aspect, the needle or needles or catheters are advanced at a pre-determined angle and depth within a patient's body and within target vasculature. Significantly, the system is effective for providing vascular access and assists with cannulation throughout the body including specifically for radiocephalic, brachio-cephalic and brachio-basilic fistulas and may range from the forearm to the upper arm or other locations on the body.

During the pre-scan, mapping and planning process, one or more of an MRI scan, a CT scan, ultrasound scan, infrared view, or 3-D photography is employed to collect information on a patient's vascular morphology and anatomy.

In various embodiments, the system can also track insertion sites, sizes, location and geometry, insertion dates, flow rates, treatment frequency and treatment length, as well as allows for patient input so that complications or infections are tracked and monitored. In certain alternative embodiments, the system can suggest insertion sites based upon a combination of historical data about the patient's previous cannula insertions with the device and the patient's anatomic imaging data, as well as in view of patient input, to provide options to the patient or healthcare provider concerning needle placement. In certain alternative embodiments, the system may also leverage crowd data from others of the system with similar anatomy and vascular morphology that had successful cannula insertion at a given site, in order to further inform the system's recommendation. Further, in alternative embodiments, the system includes a remote interface or computer that allows the patient, health care provider, or other connected health device (e.g. by Bluetooth) to enter patient health information including heart rate, blood pressure, and blood flow as well as patient diet, medication regiment, and exercise.

In alternative embodiments, the system controller manages or provides the assessment of a fistula or graft prior to cannulation. The system can be used to identify a fistula of a particular patient using ultrasound along a portion the length of a target area or a portion thereof, and using data stored in the system, recommend the location for the insertion for a present dialysis session. The recommended location could be based on many rules, including a pre-planned rotation of sites in the target area or avoidance of detected access issues. Determining the location of the system handpiece relative to the patient's arm can be done in a number of ways. In one approach optical navigation technology can be employed where one or more cameras track the system handpiece as well as the patient's arm and determine their locations. In another approach, 3D ultrasound reconstruction can be used where a combination of live ultrasound images and handpiece inertial measurements (orientation/acceleration) are compared to a stored scan of the patient's arm through artificial intelligence (AI) or machine learning (ML) models. The AI/ML models are able to determine where the handpiece is along a length of the target area.

Once the insertion site is known relative to the handpiece location, the system can direct the user to move the handpiece over an insertion site. In one particular approach, the system employs a laser or other pointer to show a technician where the insertion site should be and then the technician uses standard cannulation techniques to insert a needle or catheter. In another approach the system could use a graphical user interface to show animations which guide the user to move the handpiece appropriately.

Should an obstruction be detected, the system will prevent a cannulation procedure and can alert the patient or health care provider so that further assessment and/or intervention can be conducted. Various sensors and actuation mechanisms are provided to automate the assessment process, or portions thereof. In certain approaches, the system embodies one or more sensors that recognize thrill or vibrations, that operate like a stethoscope to track for bruit (i.e. sounds of heartbeats or blood flow), or listens to flow to look for obstructions. A microphone located in the handpiece and/or remotely connected to the handpiece could detect the pitch and amplitude of sound coming from the access. The pitch and amplitude would be compared thresholds such as known absolute limits that indicate specific access issues or changes relative to previously collected patient measurements that indicate specific access issues, or an AI/ML model which has been trained to detect the presence of specific access issues. An example implementation could be tracking a decrease in sound amplitude over multiple patient dialysis visits, which could be correlated to stenosis reducing blood flow through the access. In yet other approaches the system can use ultrasound or similar technologies to monitor the fistula diameter or cross-section area along the length of the access and/or throughout each heartbeat cycle. This information could be analyzed and compared to access issue criteria such as absolute limits, changes over time, or AI/ML models. In yet other approaches, the flow rate of blood through the access could be used to identify access issues such as stenosis or thrombosis. Ultrasound doppler sensing could allow the system to determine, peak, average, or flow rate distribution in the access or through each heartbeat cycle. Access issues could be identified by comparing this information to absolute limits. changes over time or AI/ML models.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A method of assessing health of a fistula with an ultrasound vascular access system, the method comprises the steps of:
    placing the ultrasound vascular access system against a skin above the fistula;
    controlling adjacent elements of at least one of a first ultrasound transducer array parallel to and separated from a second ultrasound transducer array when the ultrasound vascular access system is placed against the skin above the fistula;
    using the ultrasound vascular access system to identify the fistula;
    using the first ultrasound transducer array to generate a doppler signal and measure blood flow through the fistula using the doppler signal;
    assessing a characteristic of the blood flow wherein the characteristic includes at least one of blood flow velocity, volumetric blood flow rate, pulsatility and flow direction;
    using the characteristic of blood flow to assess the health of the fistula;
    using sensors to recognize vibrations coming from the fistula; and
    comparing the recognized vibrations to previously collected patient measurements.

2. The method according to claim 1 wherein the method further comprises the step of detecting a presence of one or more of a stenosis, a thrombosis, a recirculation or a hematoma.

3. The method according to claim 1 wherein the method further comprises the step of assessing a patient to determine whether the ultrasound vascular access system can be used for cannulation by moving the ultrasound vascular access system along a length of or a portion of the fistula.

4. The method according to claim 1 wherein the method further comprises the step of prompting a user to move the ultrasound vascular access system in a pattern over the fistula.

5. The method according to claim 1 wherein the doppler signal is used to determine peak, average, or flow rate distribution in the fistula.

6. The method according to claim 1 wherein one or both of the first ultrasound transducer array or the second ultrasound transducer array can be tilted with respect to a flow of blood through the fistula.

7. The method according to claim 1 wherein the method further comprises the step of prompting a user to move the ultrasound vascular access system along the fistula to assess the flow rate through the fistula.

8. The method according to claim 1 further comprising using the first ultrasound transducer array and the second ultrasound transducer array to guide alignment of a needle within the fistula.

9. The method according to claim 1 wherein the method further comprises the step of collecting imaging data to create a three-dimensional model of the fistula.

10. The method according to claim 9 wherein the method further comprises including landmarks in the three-dimensional model of the fistula.

11. The method according to claim 9 wherein the method further comprises the step of using the three-dimensional model of the fistula to identify a patient.

12. The method according to claim 11 wherein the method further comprises the step of accessing a treatment plan for the patient.

13. The method according to claim 11 wherein the method further comprises the step of accessing a treatment history for the patient.

* * * * *